(12) United States Patent  
He

(10) Patent No.: US 9,775,557 B2  
(45) Date of Patent: Oct. 3, 2017

(54) QUANTIFYING BREAST TISSUE CHANGES WITH SPECTRALLY SELECTIVE MRI AND MRS

(71) Applicant: Zhu He, Nashville, TN (US)

(72) Inventor: Zhu He, Nashville, TN (US)

(73) Assignee: VANDERBILT UNIVERSITY, Nashville, TN (US)

(*) Notice: Subject to any disclaimer, the term of this patent is extended or adjusted under 35 U.S.C. 154(b) by 599 days.

(21) Appl. No.: 14/244,462

(22) Filed: Apr. 3, 2014

(65) Prior Publication Data

US 2014/0300353 A1 Oct. 9, 2014

Related U.S. Application Data

(60) Provisional application No. 61/807,805, filed on Apr. 3, 2013.

(51) Int. Cl.

| | |
|---|---|
| *G01V 3/00* | (2006.01) |
| *A61B 5/00* | (2006.01) |
| *A61B 5/055* | (2006.01) |
| *G01R 33/485* | (2006.01) |
| *G01R 33/56* | (2006.01) |
| *G01R 33/563* | (2006.01) |

(52) U.S. Cl.
CPC .......... *A61B 5/4312* (2013.01); *A61B 5/055* (2013.01); *G01R 33/485* (2013.01); *G01R 33/5605* (2013.01); *G01R 33/5607* (2013.01); *G01R 33/56341* (2013.01); *A61B 5/4848* (2013.01)

(58) Field of Classification Search
USPC ...................................................... 324/309
See application file for complete search history.

(56) References Cited

U.S. PATENT DOCUMENTS

| | | | | |
|---|---|---|---|---|
| 5,557,202 A * | 9/1996 | Miyazaki | ........... | G01R 33/5605 324/307 |
| 5,891,032 A * | 4/1999 | Harvey | ............ | G01R 33/446 324/306 |
| 6,750,649 B1 * | 6/2004 | Rosenfeld | ............ | G01R 33/446 324/307 |
| 2006/0253015 A1 * | 11/2006 | Nezafat | ............ | G01R 33/5635 600/410 |
| 2009/0072827 A1 * | 3/2009 | Hargreaves | ........ | G01R 33/4822 324/309 |
| 2010/0156411 A1 * | 6/2010 | Setsompop | .......... | G01R 33/246 324/307 |
| 2011/0144474 A1 * | 6/2011 | Ouwerkerk | ............ | A61B 5/055 600/410 |

(Continued)

OTHER PUBLICATIONS

Atuegwu et al., "Integration of diffusion weighted MRI data and a simple mathematical model to predict breast tumor cellularity during neoadjuvant chemotherapy", MRM (2011) 66: 1689-1696.

(Continued)

*Primary Examiner* — Rodney Fuller  
(74) *Attorney, Agent, or Firm* — Nixon Peabody LLP; Eduardo J. Quinones

(57) ABSTRACT

Systems and methods for magnetic resonance analysis and imaging are provided. IN particular, pulse sequences for DWI, APT, and MRS analysis and imaging are provided which rely on an RF excitation pulse for the signal of interest, followed by one or more refocusing pulses and acquisition steps, based on the type of imaging.

15 Claims, 14 Drawing Sheets

(56) References Cited

U.S. PATENT DOCUMENTS

| | | | |
|---|---|---|---|
| 2011/0280456 A1* | 11/2011 | Sussman | G01R 33/5608 382/131 |
| 2012/0013336 A1* | 1/2012 | Hetzer | G01R 33/4818 324/309 |
| 2012/0112743 A1* | 5/2012 | Granlund | G01R 33/5614 324/309 |
| 2012/0226141 A1 | 9/2012 | Shinoda et al. | |
| 2013/0106415 A1 | 5/2013 | Cohen et al. | |
| 2014/0062474 A1* | 3/2014 | Zhou | A61B 5/055 324/309 |
| 2014/0253120 A1* | 9/2014 | Ugurbil | A61B 5/055 324/309 |
| 2014/0266195 A1* | 9/2014 | Levin | G01R 33/56509 324/309 |
| 2014/0300353 A1 | 10/2014 | He | |
| 2015/0006114 A1* | 1/2015 | Altbach | G01R 33/50 702/189 |
| 2016/0018555 A1* | 1/2016 | Jachmann | G01V 3/32 324/303 |

OTHER PUBLICATIONS

Bolan et al., "In Vivo Quantification of Choline Compounds in the Breast with 1H MR Spectroscopy", MRM (2003) 50: 1134-1143.
Cooke et al., "Quantitative proton magnetic resonance spectroscopy of the cervical spinal cord", Magnetic Resonance in Medicine (2004) 51: 1122-1128.
Kriege et al., "Efficacy of MRI and Mammography for Breast-Cancer Screening in Women with a Familial or Genetic Predisposition", N Eng K Med (2004) 351: 427-437.
Negahdar et al., "Cine phase-contrast MRI measurement of CSF flow in the cervical spine: A pilot study in patients with spinal cord injury", Medical Imaging 2011 Proc of SPIE 7965: 79652D-1-79652D-11.
Pickles et al., "A new strategy for consistent uniform fat suppression in breast MR Imaging", ISMRM (2012) 1488. (abstract).
Schar et al., "Simultaneous B0- and B1+-map Acquisition for Fast Localized Shim, Frequency and RF Power Determination in the Heart at 3T", MRM (2010) 63: 419-426.
Shemesh et al., "Longitudinal relaxation enhancement in H NMR spectroscopy of tissue metabolites via spectrally selective excitation", Chem Eur J (2013) 19: 13002-13008.
Stroman, "Magnetic resonance imaging of neuronal function in the spinal cord: Spinal fMRI", Clinical Medicine & Research (2005) 3(3): 146-156.
Sun et al., "Suppression of lipid artifacts in amide proton transfer imaging", Magnetic Resonance in Medicine (2005) 54: 222-225.
Zhou et al., "Three-dimensional amide proton transfer MR Imaging of Gliomas: Initial experience and comparison with gadolinium enhancement", J Magn Reson Imaging (2013).
Zhu et al., "Fast 3D chemical exchange saturation transfer (CEST) imaging of the human brain", Magn Reson Med (2010) 64(3): 638-644.
Abramson et al., "Current and emerging quantitative magnetic resonance imaging methods for assessing and predicting the response of breast cancer to neoadjuvant therapy", Breast Cancer: Targets and therapy (2012) 4: 139-154.
Adams, "The proteasome: A suitable antineoplastic target", Nature Reviews: Cancer (2004) 4: 349-360.
Anderson et al., "Effects of cell volume fraction changes on apparent diffusion in human cells", Magn Reson Imag (2000) 18: 689-695.
Atuegwu et al., "Integration of diffusion-weighted MRI data and a simple mathematical model to predict breast tumor cellularity during neoadjuvant chemotherapy", Man Reson Med (2011) 66: 1689-1696.
Atuegwu et al., "The integration of quantitative multi-modality imaging data into mathematical models of tumors", Phys Med Biol (2010) 55: 2429-2449.

Baek et al., "Predicting pathologic response to neoadjuvant chemotherapy in breast cancer by using MR imaging and quantitative H MR spectroscopy", Radiology (2009) 251(3): 653-662.
Baek, "Proton MR spectroscopy for monitoring early treatment response of breast cancer to neo-adjuvant chemotherapy", Annals of Oncology (2008) 19(5): 1022-1024.
Bartella et al., "Proton MR Spectroscopy with choline peak as malignancy marker improves positive predictive value for breast cancer diagnosis: Preliminary study", Radiology (2006) 239(3): 686-692.
Belli et al., "Diffusion-weighted imaging in evaluating the response to neoadjuvant breast cancer treatment", The Breast Journal (2011) 17(6): 610-619.
Bolan et al., "Imaging in breast cancer: Magnetic resonance spectroscopy", Breast Cancer Research (2005) 7: 149-152.
Chagpar et al., "Accuracy of physical examination, ultrasonography, and mammography in predicting residual pathologic tumor size in patients treated with neoadjuvant chemotherapy", Annals of Surgery (2006) 243(2): 257-264.
Charles-Edwards et al., "Diffusion-weighted magnetic resonance imaging and its application to cancer", Cancer Imaging (2006) 6: 135-143.
Choyke et al., "Functional tumor imaging with dynamic contrast-enhanced magnetic resonance imaging", J Magn Reson Imag (2003) 17: 509-520.
Danishad et al., "Assessment of therapeutic response of locally advanced breast cancer (LABC) patients undergoing neoadjuvant chemotherapy (NACT) monitored using sequential magnetic resonance spectroscopic imaging (MRSI)", NMR in BioMedicine (2010) 23: 233-241.
Dula et al., "Amide proton transfer imaging of the breast at 3T: Establishing reproducibility and possibly feasibility assessing chemotherapy response", Man Reson Med (2013) 70(1): 216-224.
Dula et al., "Development of chemical exchange saturation transfer at 7T", Magn Reson Med (2011) 66: 831-838.
Fisher et al., "Effect of preoperative chemotherapy on local-regional disease in women with operable breast cancer: Findings from national surgical adjuvant breast and bowel project B-18", Journal of Clinical Oncology (1997) 15(7): 2483-2493.
Fisher et al., "Effect of preoperative chemotherapy on the outcome of women with operable breast cancer", Journal of Clinical Oncology (1998) 16(8): 2672-2685.
Glunde et al., "Molecular and functional imaging of breast cancer", NMR in BioMedicine (2009) 22: 92-103.
Govindaraju et al., "Proton NMR chemical shifts and coupling constants for brain metabolites", NMR in BioMedicine (2000) 13: 129-153.
Holdsworth et al., "Robust GRAPPA-accelerated diffusion-weighted readout-segmented (RS)-EPI", Magn Reson Med (2009) 62: 1629-1640.
Howe et al., "Metabolic profiles of human brain tumors using quantitative in vivo H magnetic resonance spectroscopy", Magn Reson Med (2003) 49: 223-232.
Hylton et al., "Locally advanced breast cancer: MR imaging for prediction of response to neoadjuvant chemotherapy—Results from ACRIN 6657/I-SPY Trial", Radiology (2012) 263(3): 663-672.
Iacconi et al., "The role of mean diffusivity (MD) as a predictive index of the response to chemotherapy in locally advanced breast cancer", Eur Radiol (2010) 20: 303-308.
Jagannathan et al., "Evaluation of total choline from in-vivo volume localized proton MR spectroscopy and its response to neoadjuvant chemotherapy in locally advanced breast cancer", British Journal of Cancer (2001) 84(8): 1016-1022.
Jeong et al., "High-resolution human diffusion tensor imaging using 2-D navigated multishot SENSE EPI at 7T", Magn Reson Med (2013) 69: 793-802.
Johnell et al., "An estimate of the worldwide prevalence, mortality and disability associated with hip fracture", Osteoporos Int (2004) 15: 897-902.
Jones et al., "Amide proton transfer imaging of human brain tumors at 3T", Magn Reson Med (2006) 56: 585-592.

(56) References Cited

OTHER PUBLICATIONS

Jones et al., "In vivo three-dimensional whole-brain pulsed steady-state chemical exchange saturation transfer at 7T", Magn Reson Med (2012) 67: 1579-1589.
Kim et al., "Water saturation shift referencing (WASSR) for chemical exchange saturation transfer (CEST) experiments", Magn Reson Med (2009) 61: 1441-1450.
Landis et al., "Determination of the MRI contrast agent concentration time course in vivo following bolus injection: Effect of equilibrium transcytolemmal water exchange", Magn Reson Med (2000) 44: 563-574.
Le Bihan et al., "MR imaging of intravoxel incoherent motions: Applications to diffusion and perfusion in neurologic disorders", Radiology (1986) 161: 401-407.
Li et al., "DW-MRI ADC values can predict treatment response in patients with locally advanced breast cancer undergoing neoadjuvant chemotherapy", Med Oncol (2012) 29: 425-431.
Liu et al., "Neoadjuvant therapy for breast cancer", Journal of Surgical Oncology (2010) 101: 283-291.
Lobbes et al., "The roles of magnetic resonance imaging in assessing residual disease and pathologic complete response in breast cancer patients receiving neoadjuvant chemotherapy: A systematic review", Insights Imaging (2013) 4: 163-175.
Mann et al., "Breast MRI: Guidelines from the European Society of Breast Imaging", Eur Radiol (2008) 18: 1307-1318.
Manton et al., "Neoadjuvant chemotherapy in breast cancer: Early response prediction with quantitative MR imaging and spectroscopy", British Journal of Cancer (2006) 94: 427-435.
Maril et al., "Strategies for shimming the breast", Magn Reson Med (2005) 54: 1139-1145.
Meisamy et al., "Neoadjuvant chemotherapy of locally advanced breast cancer: predicting response in vivo H MR spectroscopy—A piolet study at 4 T", Radiology (2004) 233: 424-431.
Miyazaki et al., "Enhanced fat suppression technique for breast imaging", Journal of Magnetic Resonance Imaging (2013) 38: 981-986.
O'Halloran et al., "3D isotropic high-resolution diffusion-weighted MRI of the whole brain with a motion-corrected steady-state free precession sequence", Magn Reson Med (2013) 70: 466-478.
Padhani et al., "Diffusion-weighted magnetic resonance imaging as a cancer biomarker: Consensus and recommendations", Neoplasia (2009) 11(2): 102-125.
Padhani et al., "Prediction of clinicopathologic response of breast cancer primary chemotherapy at contrast-enhanced MR imaging: Initial clinical results", Radiology (2006) 239(2): 361-374.
Park, et al., "Diffusion-weighted MR imaging: Pretreatment prediction of response to neoadjuvant chemotherapy in patients with breast cancer", Radiology (2010) 257(1): 56-63.
Pauly et al., "Parameter relations for the Shinnar-Le Roux selective excitation pulse design algorithm", IEEE Transactions on Medical Imaging (1991) 10(1): 53-63.
Pickles et al., "Diffusion changes precede size reduction in neoadjuvant treatment of breast cancer", Magnetic Resonance Imaging (2006) 24: 843-847.
Pickles et al., "Role of dynamic contrast enhanced MRI in monitoring early response of locally advanced breast cancer to neoadjuvant chemotherapy", Breast Cancer Research and Treatment (2005) 91: 1-10.
Porter et al., "High resolution diffusion-weighted imaging using readout-segmented echo-planar imaging, parallel imaging and a two-dimensional navigator-based reacquisition", Magn Reson Med (2009) 62: 468-475.
Prevos et al., "Pre-treatment differences and early response monitoring of neoadjuvant chemotherapy in breast cancer patients using magnetic resonance imaging: A systematic review", Eur Radiol (2012) 22: 2607-2616.
Salhotra et al., "Amide proton transfer imaging of 9L gliosarcoma and human gliblastoma xenografts", NMR in BioMedicine (2008) 21: 489-497.

Schar et al., "Cardiac SSFP imaging at 3 Tesla", Magn Reson Med (2004) 51: 799-806.
Sener, "Neoadjuvant therapy for locally advanced cancer", Journal of Surgical Oncology (2010) 101: 282.
Sharma et al., "Longitudinal study of the assessment by MRI and diffusion-weighted imaging of tumor response in patients with locally advanced breast cancer undergoing neoadjuvant chemotherapy", NMR in BioMedicine (2009) 22: 104-113.
Shin et al., "Prediction of pathologic response to neoadjuvant chemotherapy in patients with breast cancer using diffusion-weighted imaging and MRS", NMR in BioMedicine (2012) 25: 1349-1359.
Singer et al., "H-NMR detectable fatty acyl chain unsaturation in excised leiomyosarcoma correlate with grade and mitotic activity", J Clin Invest (1996) 98(2): 244-250.
Tofts et al., "Estimating kinetic parameters from dynamic contrast-enhanced T1-weighted MRI of a diffusable tracer: Standardized quantities and symbols", J Magn Reson Imag (1999) 10: 223-232.
Turnbull et al., "Dynamic contrast-enhanced MRI in the diagnosis and management of breast cancer", NMR in BioMedicine (2009) 22: 28-39.
Van et al., "Motion-induced phase error estimation and correction in 3D diffusion tensor imaging", IEEE Transactions on Medical Imaging (2011) 30(11): 1933-1940.
Van Zijl et al., "Chemical exchange saturation transfer (CEST): What is in a name and what isn't?", Magn Reson Med (2011) 65: 927-948.
Ward et al., "A new class of contrast agents for MRI based on proton chemical exchange dependent saturation transfer (CEST_", J Magn Reson (2000) 143: 79-87.
Wenkel et al., "diffusion weighted imaging in breast MRI: Comparison of two different pulse sequences", Acad Radiol (2007) 14: 1077-1083.
Wolff et al., "Research issues affecting preoperative systematic therapy for operable breast cancer", Journal of Clinical Oncology (2008) 26(5): 807-813.
Yankeelov et al., "Integration of quantitative DCE-MRI and ADC mapping to monitor treatment response in human breast cancer: Initial results", Magnetic Resonance Imaging (2007) 25: 1-13.
Yuan et al., "Accuracy of MRI in Prediction of pathologic complete remission in breast cancer after preoperative therapy: A meta-analysis", AJR (2010) 195: 260-268.
Zhao et al., "Saturation power dependence of amide proton transfer image contrasts in human brain tumors and strokes at 3T", Magn Reson Med (2011) 66: 1033-1041.
Zhou et al., "A simple model for understanding the origin of the amide proton transfer MRI signal in tissue", Appl Magn Reson (2012) 42(3): 393-402.
Zhou et al., "Amide proton transfer (APT) contrast for imaging of brain tumors", Magn Reson Med (2003) 50: 1120-1126.
Zhou et al., "Differentiation between glioma and radiation necrosis using molecular magnetic resonance imaging of endogenous protein and peptides", Nature Medicine (2011) 17(1): 130-135.
Zhou et al., "Three-dimensional amide proton transfer MR imaging of gliomas: Initial experience and comparison with gadlinium enhancement", J Magn Reson Imag (2013) 38: 1119-1128.
Zhou et al., "Using the amide proton signals of intracellular proteins and peptides to detect pH effects in MRI", Nature Medicine (2003) 9(8): 1085-1090.
Zhu et al., "Dual-band water and lipid suppression for MR spectroscopic imaging at 3 Tesla", Magn Reson Med (2010) 63: 1486-1492.
Zhu et al., "Fast 3D chemical exchange saturation transfer (CEST) imaging of the human brain", Magn Reson Med (2010) 64: 638-644.
Zhu et al., "Spin-echo magnetic resonance spectroscopic imaging at 7T with frequency-modulated refocusing pulses", Magn Reson Med (2013) 69: 1217-1225.

* cited by examiner

100

200

300

QUANTIFYING BREAST TISSUE CHANGES WITH SPECTRALLY SELECTIVE MRI AND MRS

CROSS-REFERENCE TO RELATED APPLICATIONS

This application claims priority to and the benefit of U.S. Provisional Patent Application No. 61/807,805, filed Apr. 3, 2013 and entitled "QUANTIFYING BREAST TISSUE CHANGES WITH SPECTRALLY SELECTIVE MRI AND MRS", the contents of which are herein incorporated by reference in their entirety.

GOVERNMENT LICENSE RIGHTS

This invention was made with government support under grant numbers 1U01CA142565 and NCI P30 CA68485 awarded by the National Institutes of Health. The government has certain rights in the invention.

FIELD OF THE INVENTION

The present invention relates to quantitative MRI/MRS of breast cancer, and more specifically to apparatus and methods for spectrally selective excitation for improved DWI, APT and MRS of the breast.

BACKGROUND

Breast cancer accounts for more than 20% of newly diagnosed cancers for women worldwide. After initial diagnosis, neoadjuvant chemotherapy (NAC) is often administrated with one or more anti-neoplastic drugs to treat locally advanced breast cancer. Depending on the treatment regimen, many patients do not benefit from NAC and thus receive toxic drugs and suffer their side effects. If these patients are identified early, they will have the option of avoiding further administration of these agents and seeking alternative treatment or early surgery.

The gold standard of assessing NAC response is by histopathological examination of tumor specimens. Other forms of treatment monitoring include physical examination, mammography and ultrasound. An examination via magnetic resonance imaging (MRI), with its inherent multi-modal nature, has emerged as a platform of choice to provide several quantifiable biomarkers to monitor tissue changes during NAC. So far, frequently used magnetic resonance (MR) modalities include dynamic contrast-enhanced (DCE) MRI, diffusion-weighted imaging (DWI) and magnetic resonance spectroscopy (MRS). DCE-MRI relies on an injection of an intravenous contrast agent and continuous acquisitions of T1-weighted images as the agent perfuses into and out of a region of interest (e.g., a tumor locus). As this method has shown great sensitivity, it has become a central component of the standard-of-care breast MRI exam. However, other MR-based metrics relying on endogenous tissue contrasts are still in varying stages of technical or clinical development, specifically DWI, MRS, and amide proton transfer (APT) imaging.

DWI measures the rate of water molecules' random translation in the form of the apparent diffusion coefficient (ADC). ADC has been shown to indicate cell membrane integrity and tumor cell density. Treatment induced loss of tumor cells and increase of the extracellular space has been linked to higher ADC values during treatment. An early increase in ADC in locally advanced breast cancer may be a valuable predictor of positive outcome of NAC. Conversely, a decrease in ADC can identify non-responders. Further, Choline's role as a biomarker for cell membrane turnover has been investigated and in vivo MRS measurements of Choline and other Choline containing compounds (i.e., Choline metabolites) reflect proliferative activity of malignant cells that results in higher membrane components and elevated signals from total Choline (tCho). Early changes of tCho have been reported to occur 24 hours after the first cycle of NAC. Although general agreement has been reached regarding the usage of ADC and tCho in well-controlled clinical trials, the reliability and accuracy of these measurements are still not well established and have therefore prevented their widespread adoption in the mainstream standard-of-care setting.

APT imaging relies on a contrast generated by chemical exchange saturation transfer (CEST). Specifically, the targeted amide resonance of mobile proteins and peptides at 8.3 ppm can exchange with water protons at 4.7 ppm. Although direct observation of the amide resonance is possible, a more sensitive mechanism is to apply RF irradiation to saturate this resonance and let the saturated protons exchange with water protons. As the exchange is a continuous process, a sustained irradiation will result in a measurable decrease in the signal of water protons. The amount of signal decrease is proportional to the density of mobile proteins and peptides and depends as well on tissue pH. Therapy induced reduction of tumor cells and changes in pH should result in changes in the APT measurement. Recently, in n biopsy-proven high grade gliomas, APT-weighted images showed consistent hyperintensity even in tumors that did not display enhancement after administering a gadolinium based contrast agent. Low-grade gliomas showed iso-intensity or scattered hyperintensity, significantly lower than high-grade tumors. Additionally, APT imaging has been developed and applied in a pre-clinical study to evaluate the response to radiation therapy. Those results showed hyperintense signal with active glioma and hypointense or isointense with radiation necrosis. In summary, these early studies demonstrate APT contrast as a promising biomarker that is directly linked to the malignancy and density of tumor cells.

SUMMARY

Embodiments of the invention concern apparatus and methods for spectrally selective excitation for improved DWI, APT and MRS of the breast.

In a first embodiment of the invention, a method for a magnetic resonance (MR) analysis of a biological structure is provided. The method includes generating an imaging pulse sequence comprising a spectrally selective excitation pulse and at least one refocusing pulse subsequent to the excitation pulse, the excitation pulse selected to primarily excite water in the biological structure, subsequent to the imaging pulse sequence, collecting echo signals from the biological structure, and producing a diffusion-weighted MR image based on the echo signals.

In a second embodiment of the invention, a method for a magnetic resonance (MR) analysis of a biological structure is also provided. The method includes generating a first pulse sequence comprising at least one saturation pulse followed by a spectrally selective excitation pulse, the at least one saturation pulse selected for saturating protons for protein species in the biological structure, and the excitation pulse selected to primarily excite water in the biological structure. The method also includes applying at least one refocusing pulse and, subsequent to the applying, collecting echo signals from the biological structure. The method further includes producing an amide proton transfer MR image based on the echo signals.

In a third embodiment of the invention, a method for a magnetic resonance (MR) analysis of a biological structure is provided. The method includes generating an imaging pulse sequence comprising a spectrally selective excitation pulse and at least three refocusing pulses subsequent to the excitation pulse, the excitation pulse selected to primarily excite Choline in the biological structure and a gradient for each of the at least three refocusing pulses configured to provide spatial localization in three dimensions. The method also includes subsequent to the imaging pulse sequence, collecting echo signals from the biological structure and producing at least one of an MR image or an MR spectrum based on the echo signals. In a fourth embodiment, a magnetic resonance imaging (MRI) apparatus is provided.

The apparatus includes an MRI excitation and detection system, a display, and a controller communicatively coupled to the MRI excitation and detection system. The controller includes at least one processor and a computer readable medium having stored thereon a plurality of instructions for causing the processor to perform any of the methods of the previous embodiments.

In a fifth embodiment, there is provided a computer-readable medium, having stored therein a plurality of instruction for controlling a magnetic resonance imaging (MRI) apparatus. In the computer-readable medium, the plurality of instructions includes code sections for performing any of the methods of the previous embodiments.

BRIEF DESCRIPTION OF THE DRAWINGS

FIGS. 11A and 11B show DWI images;
FIGS. 11C and 11D show ADC maps.

DETAILED DESCRIPTION

Figure 1:
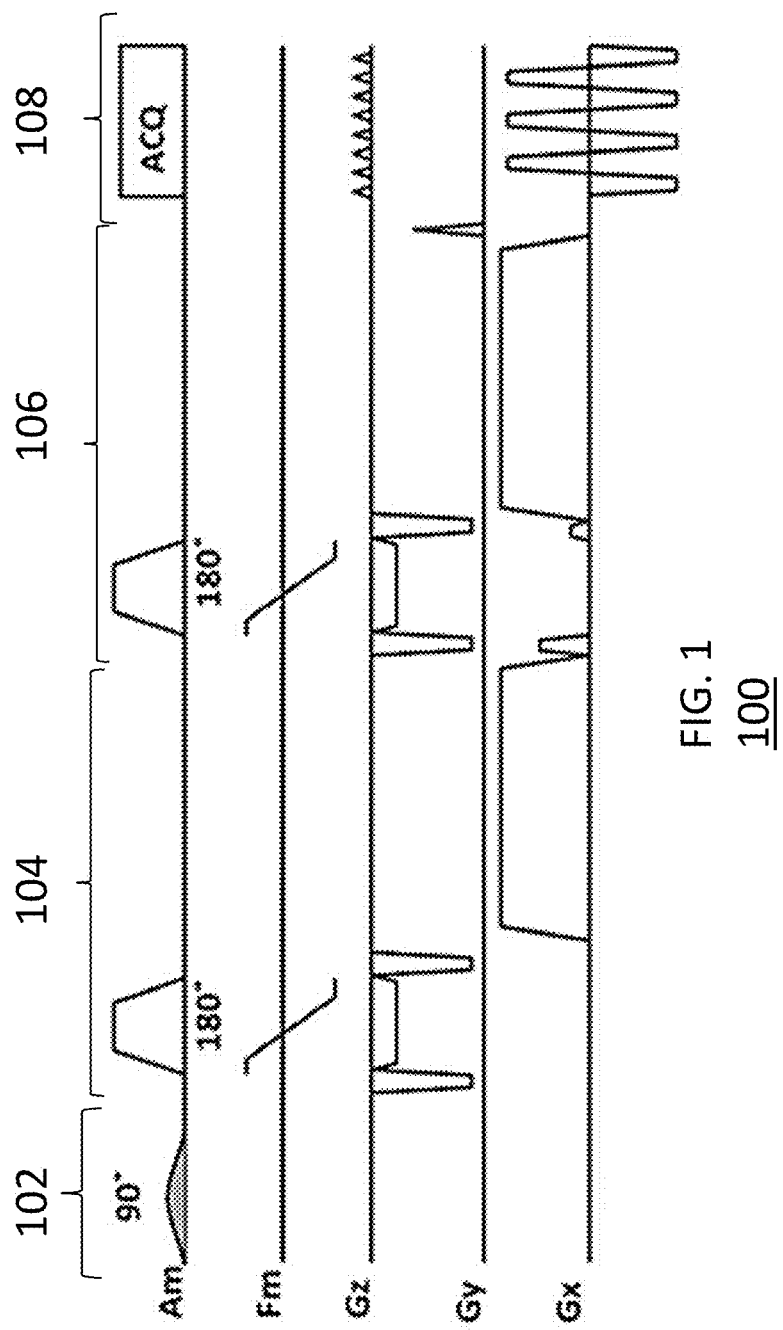
FIG. 1 shows a DWI pulse sequence in accordance with the various embodiments.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Performing DWI, APT and MRS to monitor breast cancer treatment can provide valuable information that is complementary in nature to DCE-MRI that is the standard in clinical practice. Unfortunately, many published studies for NAC treatment response have demonstrated only weak evidence of the success of imaging in distinguishing patients that respond favorably to treatment and those who do not (responders vs. non-responders). One fundamental issue is the quality and reliability of fat suppression given the pronounced susceptibility variations among air, bones as well as water and fat tissues. For DWI, the difference in water ADC at multiple time points could be attributed to a variation in residual fat signal. When asymmetry analysis is used for breast APT, unsuppressed fat signal centered at approximately −3.4 ppm (=1.3 ppm–4.7 ppm) in a z-spectrum could overwhelm the expected APT response around +3.5 ppm. As for breast MRS or tCho detection, poorly suppressed fat and water would be stronger than expected tCho signal by orders of magnitude. Accordingly, the various embodiments address these issues so that multiple biomarkers can be reliably monitored to establish their roles in the prognostic setting.

The various embodiments of the invention are directed to novel spectrally (frequency) selective excitation approaches for three breast MR techniques: diffusion weighted imaging (DWI), Choline (Cho) spectroscopy (i.e., MRS), and amide proton transfer (APT) imaging. For DWI and APT, a water-only excitation is implemented as an alternative to conventional lipid suppression. For MRS, the selectivity is placed on a narrow frequency range targeting the Cho signal to obviate the need for both water and lipid suppression. These methods result in spectrally selective approaches are robust and clinically relevant alternatives to conventional suppression-based techniques.

MRI has the unique capability to detect various tissue properties beyond morphology. In the prognostic setting, a multi-modal breast exam including DWI, MRS targeting Cho, and APT provides quantitative measurements of intrinsic tissue molecular and cellular characteristics that track tissue changes observed during the course of therapy. DWI and MRS provide uniquely valuable information on cell density and cell membrane turnover, respectively, while APT measurements can report intracellular protein degradation. Therefore, correlated measurements of DWI, MRS and APT can provide an improved biological profile of changes in breast cancer occurring during treatment.

A fundamental limitation inhibiting the routine clinical deployment of these methods in the breast tissue has been that common methods of lipid or fat suppression often fail because of heterogeneous distributions of glandular and fatty tissues. This issue, which leads to poor performance of fat suppression, contaminates quantitative measurements of water signals in MRI and Cho detection in MRS. In the case of DWI, the quantification of the water apparent diffusion coefficient (ADC) can be skewed by overlapping residual fat signal. For breast MRS targeting Cho, residual fat (and water) signals due to poor suppression may overwhelm the Cho signals. Similarly, when asymmetry analysis is used for breast APT, poorly suppressed fat signal in a z-spectrum can cause erroneous APT measurements. All these issues need to be resolved before a multi-modal breast exam can be routinely deployed in a clinical setting. Recently, water-only excitation was implemented for dynamic contrast enhanced (DCE)-MRI of the breast and showed superior results to conventional lipid suppression.

The various embodiments of the invention improve on these recent developments. In particular, the various embodiments are directed to MRI/MRS imaging using a novel set of pulse sequences for DWI, APT, and MRS which advantageously utilize spectrally selective excitation.

The pulse sequences of the various embodiments provide a departure from the traditional formula of pre-saturation followed by excitation that has been used in MRI and MRS for decades. In particular, the various embodiments of the invention are directed to a novel category of sequences that employ radio frequency (RF) excitations that only affect the signal source to be acquired. In contrast, conventional MRI imaging relies on either suppression of signal types or excitation of multiple types of signal source. Thus, the various embodiments of the invention provide pulse sequences for DWI, APT, and MRS imaging and analysis which rely on an RF excitation pulse for the signal of interest (i.e., species of interest, such as water or Choline), followed by sequence of one or more refocusing pulses and acquisition steps, based on the type of imaging.

With regards to DWI, a conventional pulse sequence for breast tissues is similar to that of DWI for brain tissues. That is, there is typically an excitation pulse targeting water and fat that is combined with some type of suppression procedure, particularly suppression of fat. In the case of brain tissues, the amounts and locations of different types of tissues are fair constant from subject to subject. However, the deficiency of this methodology is that the amount of fat can vary substantially from one subject to another in breast tissues. As a result, in subjects with high amounts of fat in breast tissues, the usefulness of such a scan decreases. To address this deficiency, a new DWI pulse sequence is provided, as shown in FIG. 1.

As shown in FIG. 1, the new DWI sequence 100 consists of an excitation pulse 102, followed by one or more refocusing pulses (104 and 106). In the various embodiments, a refocusing pulse 104, 106 can be accompanied by gradients (Gx, Gy, Gz), as shown in FIG. 1. Thereafter, MRI acquisition 108 is performed. In the various embodiments, the excitation pulse 102 is selected to be a 90 degree excitation pulse configured (in terms of duration and bandwidth) to excite all water signals with a minimal amount of lipid contamination. This is performed via use of spectrally (frequency) selective excitation pulses. In the various embodiments, the excitation pulse 102 can have an amplitude between 0.1 µT and 30 µT, such as between 0.1 µT and 3 µT or 0.3 µT and 2 µT, a center frequency less than 12.0 ppm, such as between 2.5 ppm and 7.0 ppm or between 3.2 ppm and 6.2 ppm), a bandwidth between 20 Hz and 525 Hz (such as between 60 Hz and 385 Hz), and a duration between 4 ms and 100 ms (such as between 5.5 ms and 35 ms). Further, the excitation pulse can be a Gaussian pulse, a sinc Gaussian pulse, a minimal phase pulse, or an adiabatic half passage (AHP) pulse. The MRI acquisition (108) can then be performed using a single slice, single shot echo planar imaging (EPI) method, a 2D or 3D multi-shot EPI method or any fast imaging methods.

In some embodiments, the refocusing pulses 104 and 106 can be implemented using at least one conventional RF refocusing pulse. However, in other embodiments, an adiabatic inversion pulses, such as adiabatic full passage (AFP) pulses of various types (such as hyper secant (HS) or FOCI), can be utilized. When utilizing a pulse designed to provide excitation of water-only (i.e., via frequency selection), the pulse ends up exciting water everywhere. As a result, no spatial selectivity is provided with excitation. This can cause the occurrence of artifacts and other unwanted features in the final image, i.e., the resulting image will be unclear. Pairs of adiabatic inversion pulses, such as AFP refocusing pulses, can be utilized to alleviate these issues and provide a more accurate spatial localization. In particular, AFP pulses of the HS shape or otherwise operate by uniformly rotate the magnetization vector, even when the B1 field is spatially non-uniform. In other words, pairs of AFP pulses are useful for addressing the inhomogeneity typical for MRI of breast tissues. Since AFP refocusing pulses have to work in pairs and they tend to consume more RF power, their occurrences in a pulse sequence need to be limited. In the various embodiments, the AFP pulses are suitable for DWI because DWI sequences generally do not require the formation of more than one echo.

With regards to APT, the concerns leading to the development of the new DWI sequence of FIG. 1 also apply. In APT, the goal is to obtain a measurement of protein content in tissues via an indirect measurement. In particular, this is performed via an analysis of the exchange of protons between water and the proteins. This process begins by saturating the proteins, i.e., disturbing or exciting the protons in the proteins. As a result of this saturation, the protons are susceptible to exchange with other species. In the case of tissues including proteins and water, a portion of these protons will eventually exchange with water molecules. Thereafter, upon excitation of water, the proton exchange will affect the amount of water that can be excited. This amount will be proportional to the amount of protein in the tissues. In conventional methods, similar to DWI, APT typically includes, in addition to the saturation of proteins, an excitation pulse targeting water and fat combined with some type of suppression procedure for the suppression of fat.

However, as with DWI, the amount and distribution of fat varies from subject to subject and cannot be accurately predicted in breast tissues. Thus, conventional excitation/suppression processes for APT are generally unsuitable for performing useful APT for breast tissue. To address this deficiency, a new APT pulse sequence is provided, as shown in FIG. 2, that consists of pseudo continuous wave (CW) saturation and a water only excitation with a gradient spin echo (GRASE) sequence.

Figure 2:
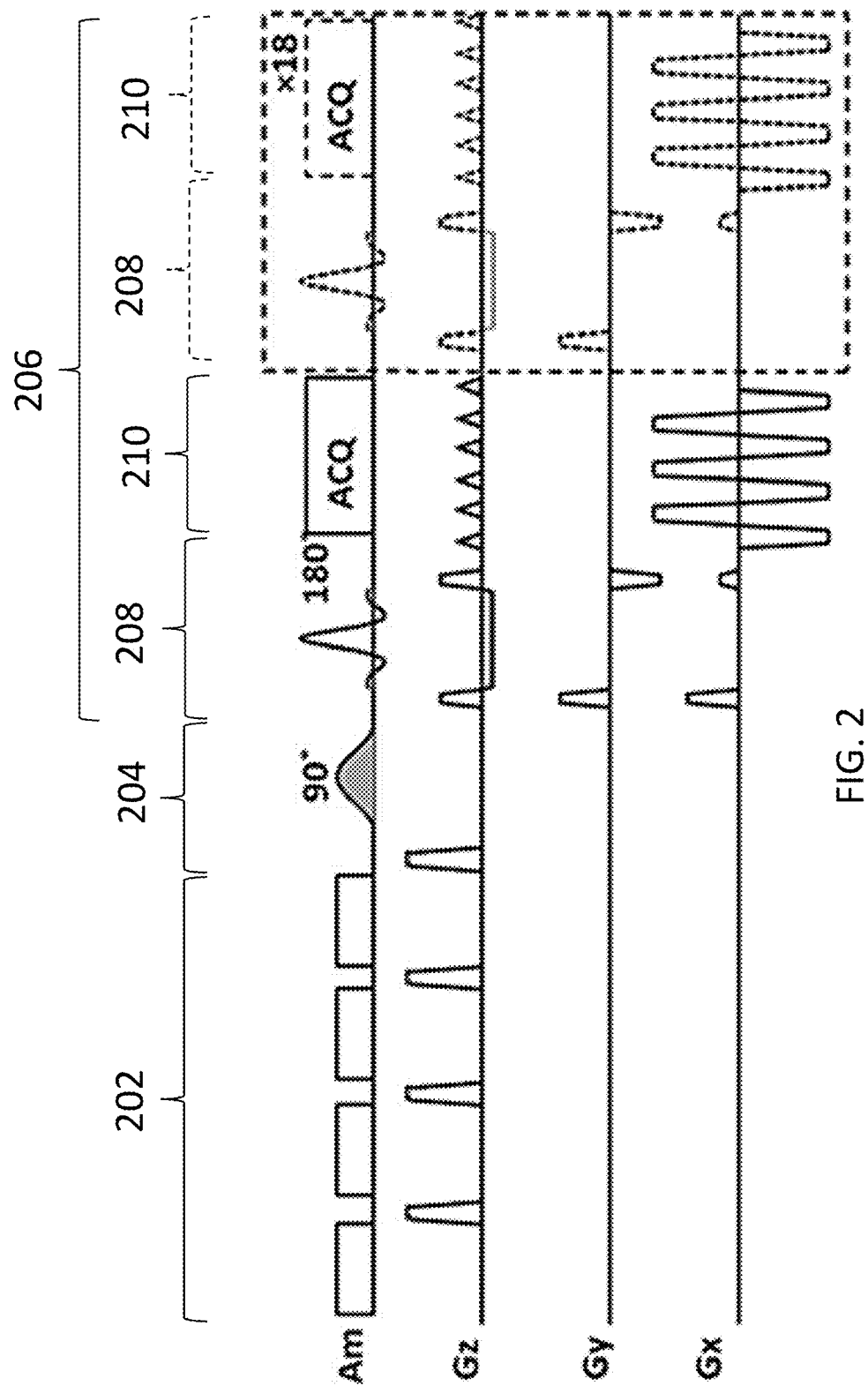
FIG. 2 shows an APT pulse sequence in accordance with the various embodiments.

As shown in FIG. 2, the new APT sequence 200 consists of a saturation sequence 202 to provide the saturation of the proteins. The saturation sequence 202 can be a conventional saturation sequence or any other sequence, such as described in these references: Zhu H, Jones C K, van Zijl P C, Barker P B, Zhou J., "Fast 3D chemical exchange saturation transfer (CEST) imaging of the human brain", Magn Reson Med 2010, 64(3):638-644 and Zhou J, Zhu H, Lim M C, Blair L, Quinones-Hinojosa A, Messina S, Eberhart C G, Pomper M G, Laterra J, Barker P B, Van Zijl P, Blakeley J., "Three-Dimensional Amide Proton Transfer MR Imaging of Gliomas: Initial Experience and Comparison With Gadolinium Enhancement", J Magn Reson Imaging 2013. This is then followed by an excitation pulse 204, targeting water. In the various embodiments, the excitation pulse 202 is selected to be a 90 degree excitation pulse configured (in terms of duration and bandwidth) to excite all water signals with a minimal amount of lipid contamination, similar to that utilized for DWI with respect to FIG. 1. However, the various embodiments are not limited in this regard and the pulses can be different, as long as they remain selective to water. Following the excitation pulse 204, a refocusing/acquisition (R/A) sequence 206 is performed.

In the various embodiments, the R/A sequence 206 is structured to provide a sequence similar to a fast spin echo sequence. That is, repeatedly applying a refocusing pulse 208 followed by an MRI acquisition 210. In the various embodiments, the refocusing pulse 208 can be accompanied by gradients (Gx, Gy, Gz), as shown in FIG. 1. In the exemplary configuration of FIG. 2, the R/A sequence can be repeated 18 times. However, the number of times the R/A sequence is performed can vary depending on the imaging parameters. Thus, the R/A sequence can be performed a single time or multiple times in the various embodiments. However, a range of 10 to 30 repetitions is useful in most cases. The MRI acquisition 210 can then be performed using any conventional methods. As to the refocusing pulse sequence 208, the refocusing can be performed using conventional RF refocusing pulses or a combination of pair(s) of AFP refocusing pulses and conventional refocusing pulses, to address the inhomogeneity typical for MRI of breast tissues, as described above with respect to FIG. 1.

With regards to MRS, concerns similar to those leading to the development of the new DWI and APT sequences of FIGS. 1 and 2 also apply. As noted above, the goal in MRS to obtain a measurement of Choline or any other particular chemical compounds which are generally elevated in malignant breast tumor tissues. Conventional MRS of breast tissue typically consists of point resolved spectroscopy (PRESS), which consists typically of an excitation pulse, which excites all types of species, followed by two refocusing pulses prior to acquisition. In PRESS, the sequence preceded by a suppression of water and fat to prevent these signals from overwhelming the signal from Choline or any other particular chemical compounds. However, in the case where the amount and distribution of fat and water cannot be accurately determined, such as in breast tissues, fat and water may be poorly suppressed. Thus, the detection of Choline or any other particular chemical compounds becomes difficult, as the signal from water and fat overwhelms the signal of the chemical compound of interest. To address the deficiencies of PRESS, the various embodiments provide a new MRS sequence (PRESS) with excitation restriction (ER) or PRESSER. The PRESSER pulse sequence is shown below in FIG. 3. Although the exemplary embodiments will be described below with respect to Choline, the various embodiments are not limited in this regard. Rather as noted above, the techniques described herein can be utilized with one or more chemical compounds of interest.

Figure 3:
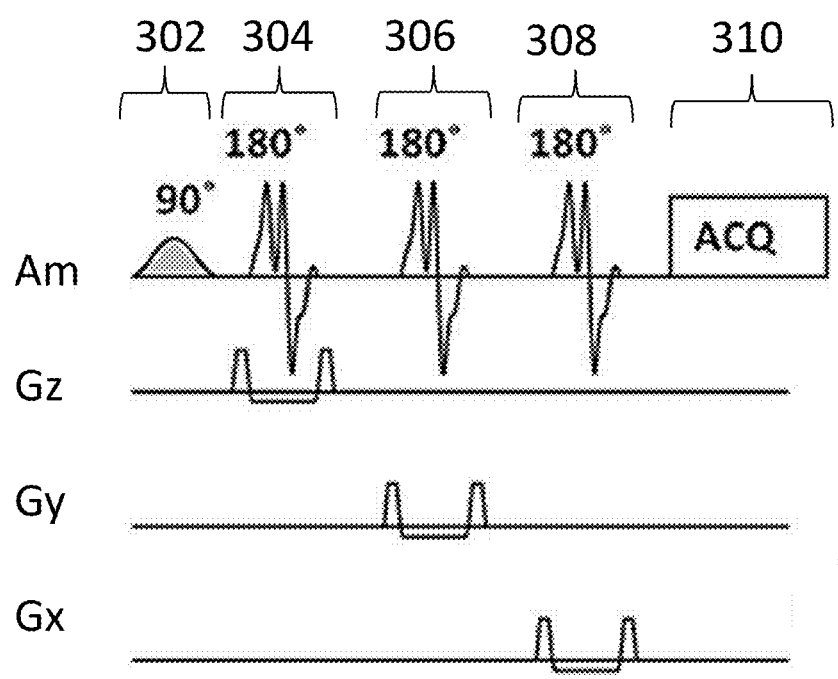
FIG. 3 shows an MRS pulse sequence in accordance with the various embodiments.

As shown in FIG. 3, the PRESSER pulse sequence 300 includes first providing a Choline excitation pulse 302. In the various embodiments, the Choline excitation pulse is configured to excite Choline. In the various embodiments, the Choline-only excitation pulse 302 is configured similar to the water-only excitation pulses for FIGS. 1 and 2. That is, the pulse 302 is selected to be a 90 degree excitation pulse configured (in terms of duration and bandwidth) to excite all Choline signals with a minimal amount of water or fat excitation. In the various embodiments, the excitation pulse 302 can have an amplitude between 0.06 µT and 1.5 µT (such as between 0.05 µT and 0.7)µT, a center frequency between 2.0 ppm and 4.5 ppm (such as between 2.5 ppm and 3.5 ppm), a bandwidth between 10 Hz and 260 Hz (such as between 50 Hz and 130 Hz), and a duration between 8.5 ms and 160 ms (such as between 15 ms and 45 ms). The excitation pulse 302 can then be followed by a first refocusing pulse sequence 304, a second refocusing pulse sequence 306, and a third refocusing pulse sequence 308. Thereafter, MRI acquisition 310 is performed. The MRI acquisition 310 can then be performed using any acquisition method for spectroscopy and spectroscopic imaging.

As to the refocusing pulse sequences 304, 306, 308, the refocusing pulses can be performed using conventional RF refocusing pulses or AFP refocusing pulses, to address the inhomogeneity typical for MRI of breast tissues, as described above with respect to FIG. 1. However, in contrast to the refocusing pulse sequence of FIG. 1, the refocusing pulse sequences 304, 306, and 308 are not identical. Rather, the refocusing pulses 304, 306, and 308 are designed to provide spatial localization in 3 dimensions. As shown in FIG. 3, this is accomplished by applying a different magnetic field gradient during each of the refocusing pulses. For example, as shown in FIG. 3, each of the pulses 304, 306, 308 is accompanied by a gradient in a different direction.

Figure 4A:
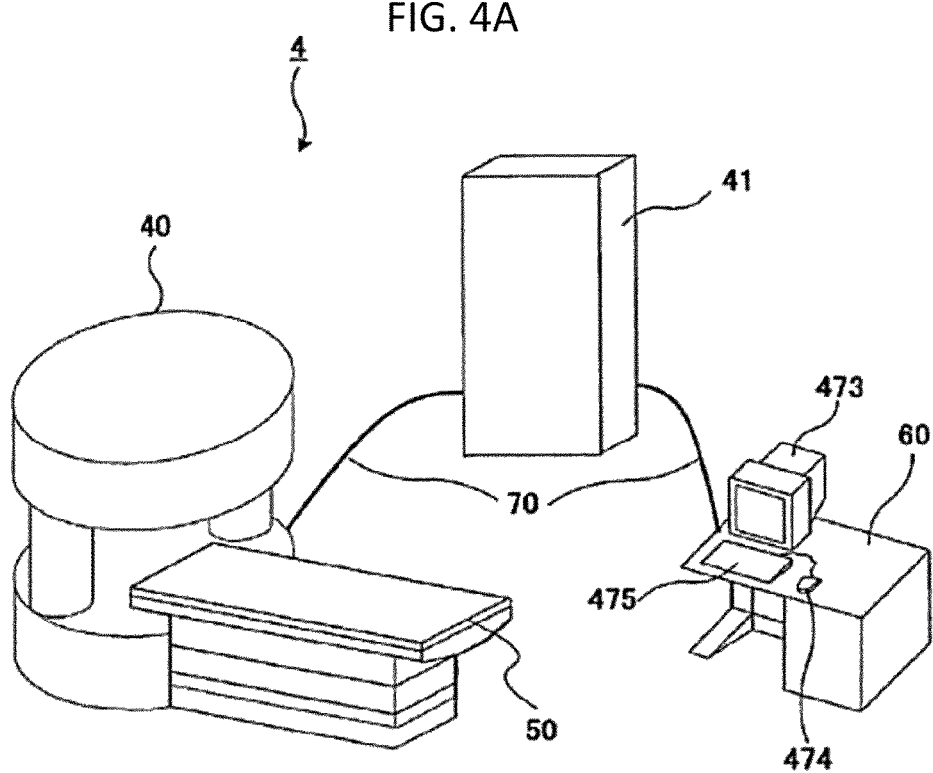
FIG. 4A is a structural diagram showing an MRI apparatus in accordance with the various embodiments.
Figure 4B:
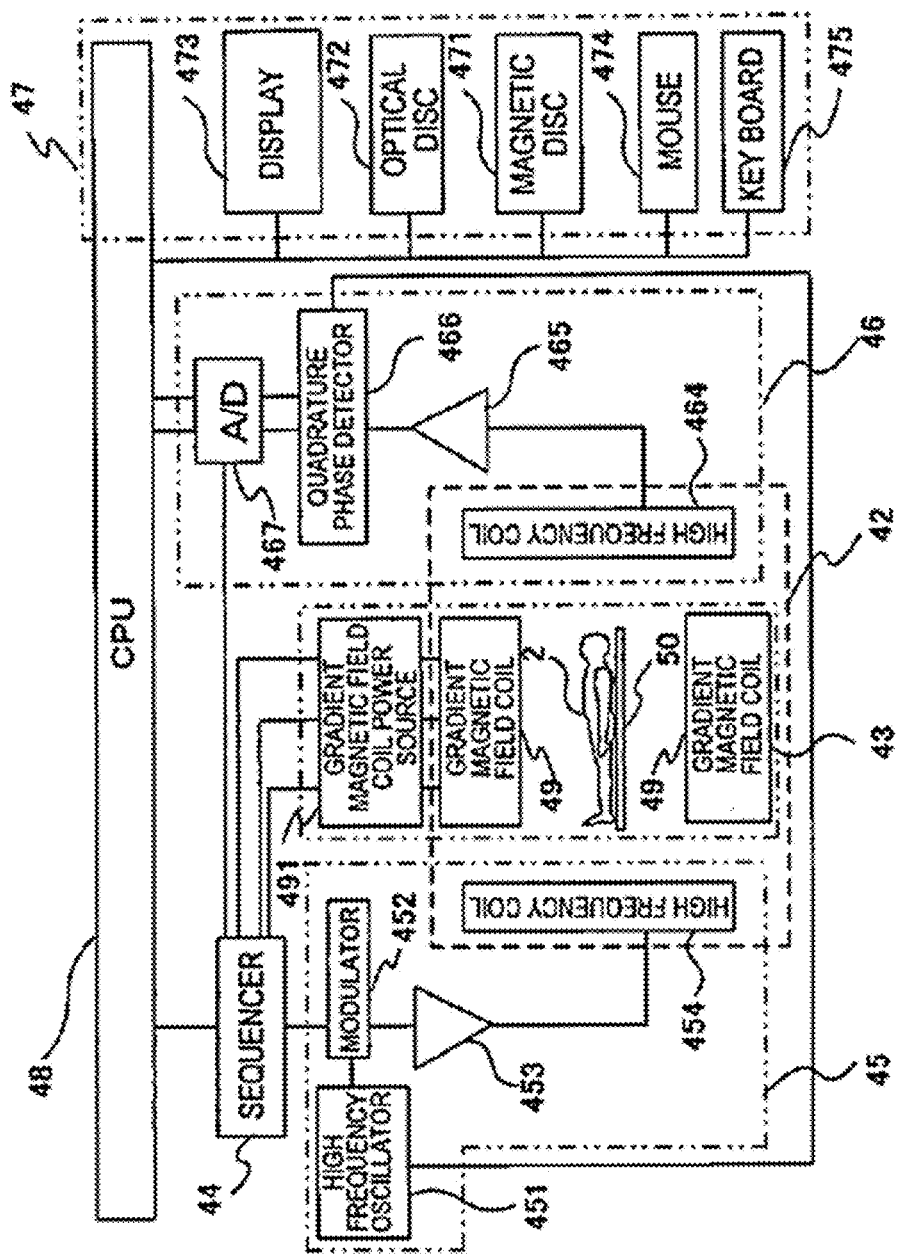
FIG. 4B is a block diagram to show the interior of the MRI apparatus in FIG. 4A.

Now turning to FIGS. 4A and 4B, an MRI apparatus configured for carrying out the various embodiments of the invention will be described. FIG. 4A is a structural diagram showing an MRI apparatus in accordance with the various embodiments, and FIG. 4B is a block diagram to show the interior of the MRI apparatus in FIG. 4A.

The MRI apparatus 4 of FIG. 4A is of a perpendicular magnetic field type (open type), but may be of any other type such as a tunnel type. In the MRI apparatus 4, an oscillating magnetic field (electromagnetic waves) is applied to a subject arranged in static magnetic fields to induce nuclear magnetic resonance (NMR). A detecting coil (RF coil) detects resonance signals as electrical signals, thereby the signals are reconstructed as projected data to produce an image of the interior of the subject 2 noninvasively.

The MRI apparatus 4 comprises a gantry 40, a house 41 in which a power source to drive various devices in the gantry 40 and various control devices to control are stored, a bed 50 on which the above subject 2 is rested, and a processing unit 60 which processes the received NMR signals to reconstruct a tomogram image of the subject 2. The gantry 40 and the house 41 are connected by a power source/signal line 70. Similarly, the processing unit 60 and the house 41 are connected by a power source/signal line 70.

The gantry 40 and the bed 50 are placed in a shield room to shield high frequency electromagnetic waves and static magnetic fields (not shown). The house 41 and the processing unit 60 are placed outside of the shield room.

Next, referring to FIG. 4B, the structure of an exemplary MRI apparatus 4 for carrying out the various embodiments of the invention will be explained in more detail. The MRI apparatus 4 includes a static magnetic field generating system 42, a magnetic field gradient generating system 43, a sequencer 44, a transmitting system 45, a receiving system 46, a signal processing system 47 including an operating section, and a central processing unit (CPU) 48. The static magnetic field generating system 42 generates a uniform static magnetic field around the subject 2 in a direction of the body axis of the subject 2 or in a direction orthogonal to the body axis of the subject 2. The static magnetic field generating system 42 comprises permanent magnet type, resistive type or superconductive type magnetic field generating means placed in the extended space around the subject 2.

The magnetic field gradient generating system 43 comprises two gradient magnetic field coils 49 which are wound in the three X, Y and Z axis directions, and a gradient magnetic field power source 491 to drive each gradient magnetic field coils 49. When the gradient magnetic field coil power source 491 for each gradient magnetic field coils 49 is driven by a command from the sequencer 44, gradient magnetic fields GX, GY, and GZ in the three X, Y and Z axis directions are applied to the subject 2. The way to apply the gradient magnetic fields sets a slice plane relative to the subject 2.

The sequencer 44 repeatedly applies high frequency magnetic field pulses which cause the atomic nucleus of an atom that produces a living tissue of the subject 2 to induce nuclear magnetic resonance, in a predetermined pulse sequence, as described in greater detail below. The sequencer 44 is controlled to operate by the CPU 48, and sends various commands required to collect data of tomogram images of the subject 2 to the transmitting system 45, the magnetic field gradient generating system 43, and a receiving system 46.

The transmitting system 45 irradiates a high frequency magnetic field which causes the atomic nucleus of an atom that produces a living tissue of the subject 2 to induce nuclear magnetic resonance with a high frequency pulses emitted from the sequencer 44. The transmitting system 45 includes a high frequency oscillator 451, a modulator 452, a high frequency amplifier 453, and a high frequency coil 454 for transmitting. The high frequency pulses emitted from the high frequency oscillator 451 are amplitude modulated by the modulator 452 according to the command from the sequencer 44. After the amplitude modulated high frequency pulses are amplified by the high frequency amplifier 453, the pulses are supplied to the high frequency coil 454 positioned close to the subject 2. In this way, an electromagnetic wave is irradiated to the subject 2.

The receiving system 46 detects an echo signal (NMR signal) emitted by the nuclear magnetic resonance in atomic nucleus of the living tissue of the subject 2. The receiving system 46 comprises a high frequency coil 464 for receiving, an amplifier 465, a quadrature phase detector 466, and an A/D converter 467. The electromagnetic wave (NMR signal) from the subject 2 in response to the electromagnetic waves emitted from the high frequency coil 454 for transmitting is detected by the high frequency coil 464 positioned close to the subject 2. The detected NMR signal is input into the A/D converter 467 via the amplifier 465 and the quadrature phase detector 466 to be converted into a digital signal. The quadrature phase detector 466 converts the detected NMR signal into biserial data collected by sampling at timings specified by the command from the sequencer 44. The collected data is transmitted to the signal processing system 47.

The signal processing system 47 includes a CPU 48, a recording device such as a magnetic disc 471 and an optical disc 472, a display 473 such as a CRT, a pointing device and its controller such as a mouse 474, and an input unit such as a key board 475. The CPU 48 performs a Fourier transform operation and an operation of correction coefficient calculation for image reconstruction, and performs appropriate operations based on a signal strength distribution or a plurality of signals of any section to obtain a distribution to create an image, thereby generates a tomogram. The display 473 displays the tomogram.

Such a MRI apparatus 4 with the recent increased performance produces a high magnetic field (e.g. 1.5 T or greater) apparatus, which allows four dimensional image data to be obtained with noise of a practical level and high time resolution.

Although FIGS. 4B and 3C describe an exemplary MRI system including a specific set and arrangement of components, this is solely for illustrative purposes and the various embodiments are not limited in this regard. Rather, an MRI system configured in accordance with the various embodiments can have more or less components than illustrated in FIGS. 4A and 4B. Further, the arrangement of such components of an MRI system can be the same or different as that described with respect to FIGS. 4A and 4B. For example, the system in FIGS. 4A and 4B is shown to be an open MRI system. However, the various embodiments can also be utilized with a closed or conventional MRI system.

EXAMPLES

The following examples and results are presented solely for illustrating the various embodiments and are not intended to limit the various embodiments in any way.

All MRI and MRS scans were performed on a 3T whole body scanner (Achieva, Philips Healthcare, Best, the Netherlands) with a 16 channel phased array breast coil (Mammotrak, InVivo Corp. Gainesville, Fla.). All subjects were healthy volunteers.

A. Selection of Excitation Profile Using PRESSER.

Figure 5A:
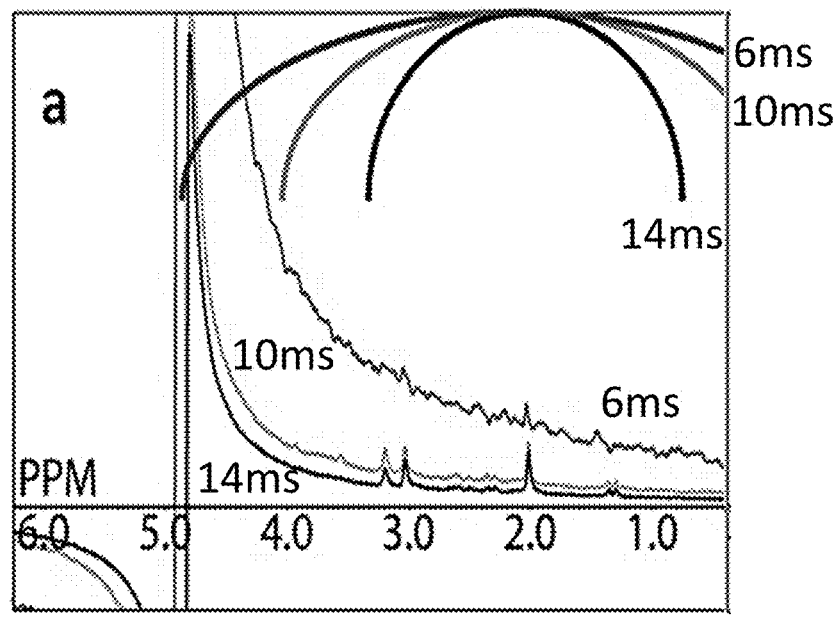
FIG. 5A shows a spectral comparison of varying excitation pulse duration of PRESSER for a phantom water-only excitation with varying pulse durations.
Figure 5B:
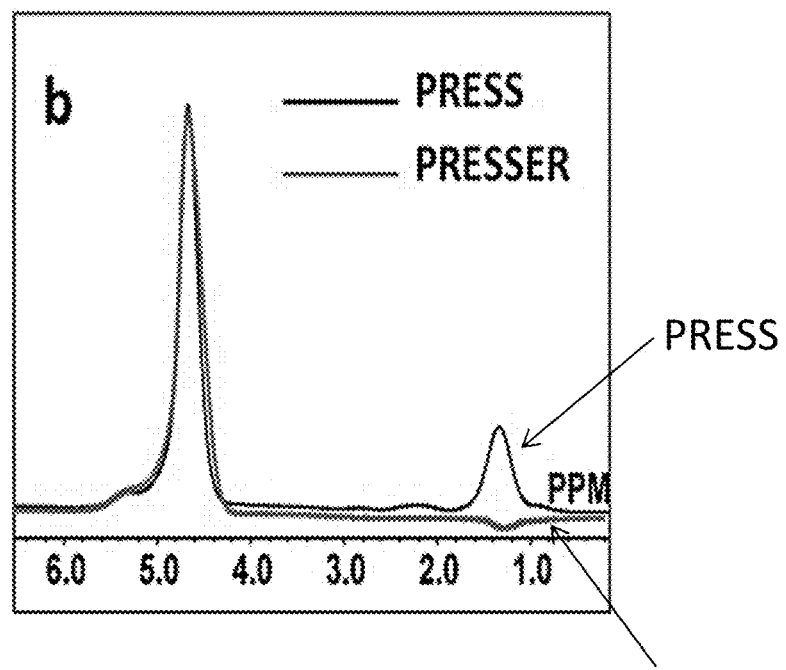
FIG. 5B shows a spectral comparison of PRESS and PRESSER for in vivo water-only excitation in accordance with the various embodiments.

Accurate implementation of water-only excitation was initiated with a proper evaluation of the selectivity of the excitation pulse. The goal was to determine optimal duration (and bandwidth) of the 90° pulse to excite all water signals at 4.7 ppm with the minimal amount of lipid contamination. Since lipid signals in breast adipose tissues consist of several resonances at 0.9 ppm, 1.3 ppm, 2.1 ppm, 2.7 ppm, 4.3 ppm and 5.4 ppm, initial testing was performed using a spectroscopic phantom consisting of a solution of neuro-metabolites with spectral peaks in the same range. The center frequency of the excitation was placed at the approximate center of the lipid region (2.0 ppm) while the duration of the pulse was varied from 6 ms to 16 ms in 2 ms increments. Three acquired spectra are plotted in FIG. 5A. The remaining acquisition parameters were TE/TR=61 ms/2 s, NSA=16, scan time=34 sec. The phantom results show that as the pulse duration increased, a diminishing spectral range was acquired at around 2.0 ppm. Specifically, when the duration was 10 ms (with bandwidth of 213 Hz), spectral peaks at 3.2, 3.0 and 1.4 ppm were visible. This configuration was then tested in vivo where a sagittal volume was prescribed to match the coverage of DWI or APT sequences. Standard PRESS and PRESSER were performed with center frequency on water. FIG. 5B shows that PRESSER acquired a nearly identical water signal with minimal erroneous lipid signals resulting from their dominant resonance at 1.3 ppm. The excitation duration of 10 ms was used to acquire all the water-only DWI and APT results shown below.

B. Shim Optimization and Center Frequency Selection for Frequency Selective Excitation.

Figure 6:
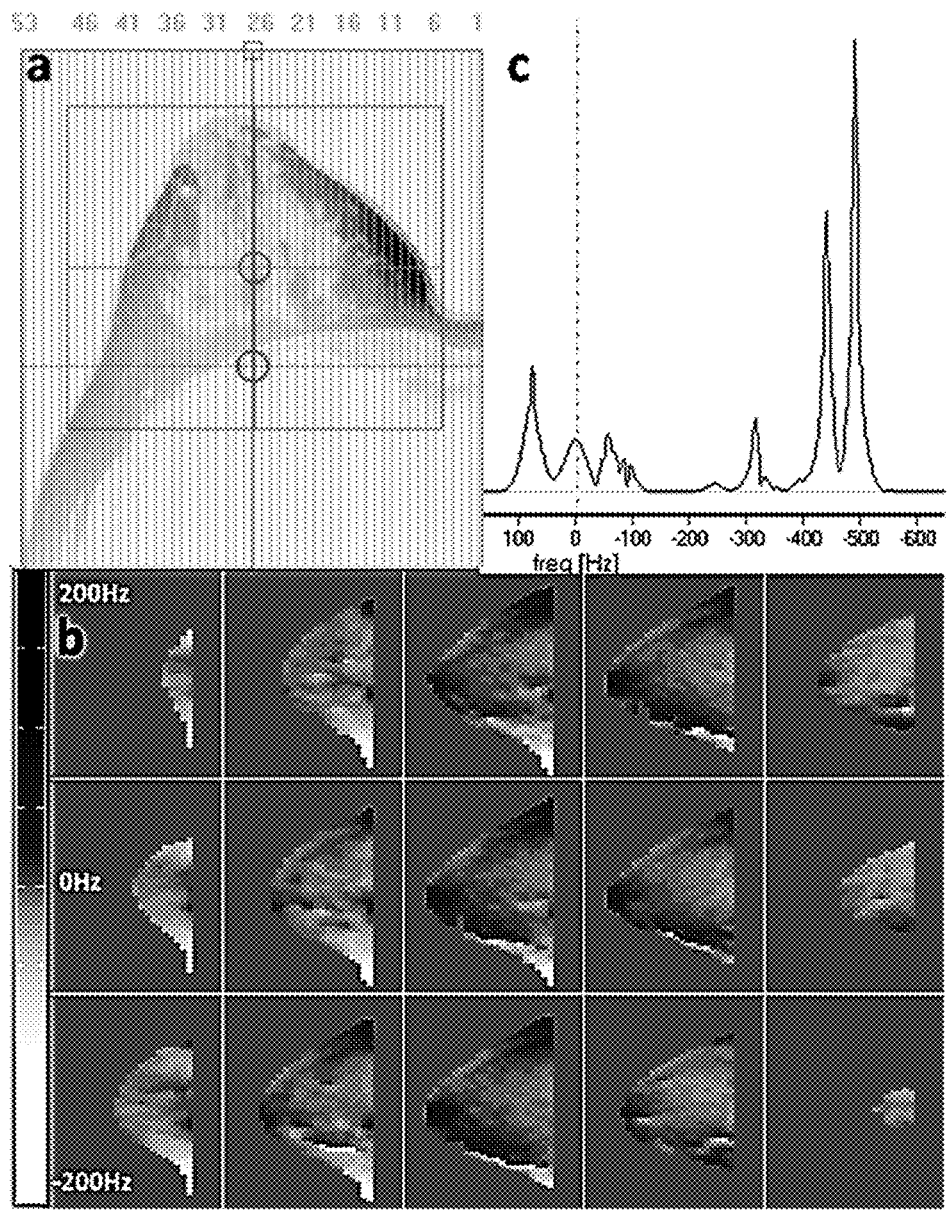
FIG. 6 illustrated a method of field map based shimming and center frequency determination.

The frequency selective methods of the various embodiments depend on accurate shimming and center frequency determination. To achieve this goal reliably and reproducibly, a unilateral, sagittal 3D phase map acquisition (Panel a in FIG. 6) was prescribed to cover the breast. The scanner's automatic volume shimming was used for this acquisition and consists of a 3D fast gradient echo sequence with two echo times of 4.6 ms and 6.9 ms. The $\Delta TE$ of 2.3 ms resulted in in-phase signals of water and fat signals shown in (Panel b in FIG. 6). The other parameters were: FOV=16 $cm^3$, voxel size=3 $mm^3$, imaging matrix=$64^3$, TR=11 ms, and total scan time was 29 seconds. The shim optimization procedure was performed for 1st and 2nd order terms combined. Before any measurement proceeded with the optimized shim parameters, the center frequency determination was performed to identify water resonance. Specifically, the entire ROI was acquired with a standard SV PRESS sequence. The resulting full spectrum was displayed on the scanner console (Panel c in FIG. 6). In majority of the cases where lipid signal in the ROI was much stronger than water signal, the scanner operator manually identified water peak as center frequency.

C. DWI Breast Imaging with Water-Only Excitation.

Figure 7:
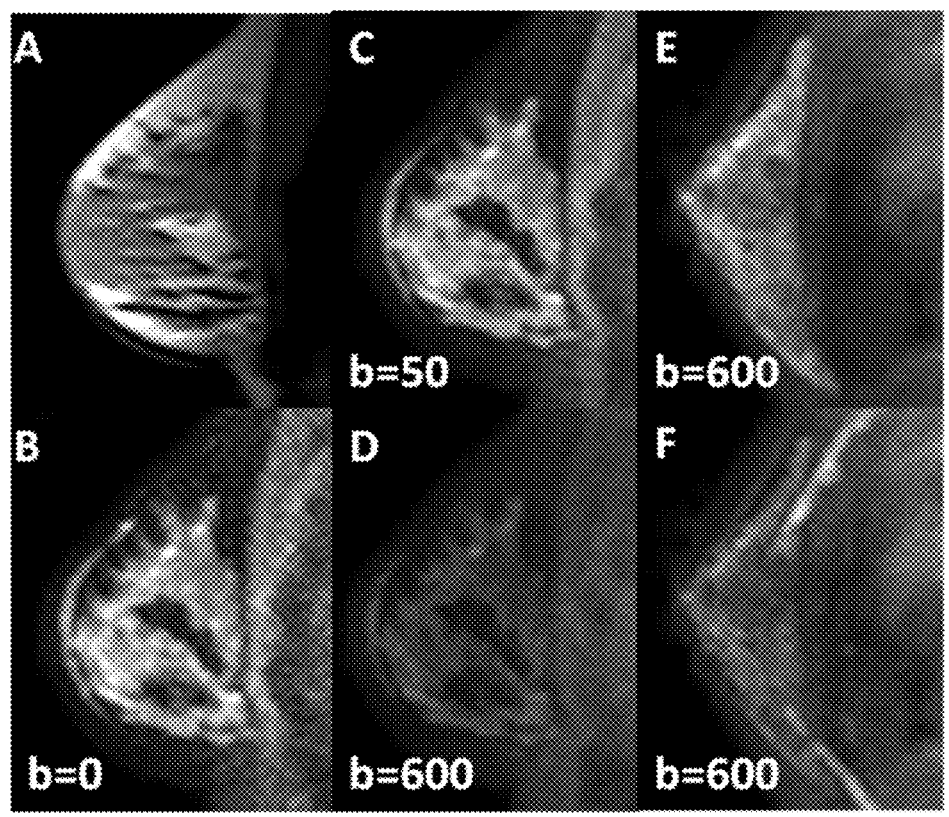
FIG. 7 shows image results for a survey image (Panel A) versus water-only DWI images with varying b-factors (Panels B, C, D) and a comparison of a water-only DWI image (Panel E) and a conventional DWI image with fat suppression (Panel F)

The combination of advanced shimming and proper excitation profile on water resonance are crucial to the success of the water-only DWI method. To further improve the method's performance, conventional RF refocusing was replaced by two AFP pulses as discussed above, to compensate for the loss of slice selection by the excitation pulse. In particular, spectrally selective excitation was implemented a spin echo (SE) based pulse sequences. Unlike the gradient echo sequences, where the only RF pulse was modified to be spectrally and spatially selective, SE based sequences were used to test the same concept with frequency selective excitation and slice-selective refocusing pulses. Specifically, for DWI, a sinc-Gaussian (SG) pulse with a bandwidth (BW) of 200 Hz was combined with two adiabatic full passage (AFP) pulses (5.8 ms duration and 2.5 kHz BW). The other acquisition parameters were: TE/TR=76 ms/1 s, slice thickness=3 mm, FOV=(192 mm)$^2$ (FH×AP), resolution=(2 mm)$^2$, b-factors=0, 50, and 600 s/mm$^2$, NSA=10, scan time=1:41 min. During in vivo testing, water-only DWI and conventional DWI with lipid suppression were compared in co-registered scans. FIG. 7 shows a survey image in A and water-only DWI images in B, C, and D, where b=0, 50 and 600 s/mm$^2$. E and F in FIG. 7 compare images of water-only DWI and standard DWI with fat suppression. As can be readily observed from FIG. 7, the water-only DWI method clearly exceeds the conventional method in terms of the depiction of glandular tissue details.

D. APT Imaging from the Brain to the Breast

As noted above, the majority of the in vivo CEST methods employ a pulsed CEST method that relies on fast repetitions of RF saturation at the amide resonance and 3D gradient echo imaging with small flip angles. In this study, the alternate method that consists of pseudo continuous wave (CW) saturation and a 3D image acquisition with a gradient spin echo (GRASE) sequence was used. Compared to the pulsed approaches, this method prepares maximal contrast after approximately 1 s of RF saturation (the longest possible using the 3T scanner's body coil for transmission). In particular, as described above, the 3D GRASE acquisition consists of only one 90° pulse immediately after the RF saturation. The only excitation pulse in the GRASE sequence captures z magnetization with the maximal amount of saturation and rotates all of it into the transverse plane for acquisition.

In a pilot study for brain tumor staging, the APT method with standard slice selective excitation was employed. Specifically, this sequence consists of three sections: RF saturation (4 block pulses of 200 ms duration and 2 $\mu T$ amplitude); lipid suppression (to be improved with water-only excitation); and 3D GRASE image acquisition. It was demonstrated previously that a saturation power of 2 $\mu T$ causes an optimal hyperintense APT-MRI signal in the tumor compared with approximately isointense normal brain tissue. The APT signal was measured by an asymmetry analysis of magnetization-transfer-ratio (MTR) between signal intensities of ±3.5 ppm with respect to the water frequency. The water saturation shift referencing (WASSR) method was used to determine $B_0$ maps (range=−1.5 to 1.5 ppm; interval=0.125 ppm; saturation power=0.5 $\mu T$; saturation time=200 ms; repetition time=1.25 s; scan time=2 min 15 s). To correct for residual $B_0$ inhomogeneity effects, APT imaging was acquired with a six-offset protocol (S0, ±3, ±3.5, ±4 ppm from water, with respective numbers of averages of 1, 1, 4, and 1). More averages at ±3.5 pm were prescribed to increase the SNR of APT contrast.

Figure 8:
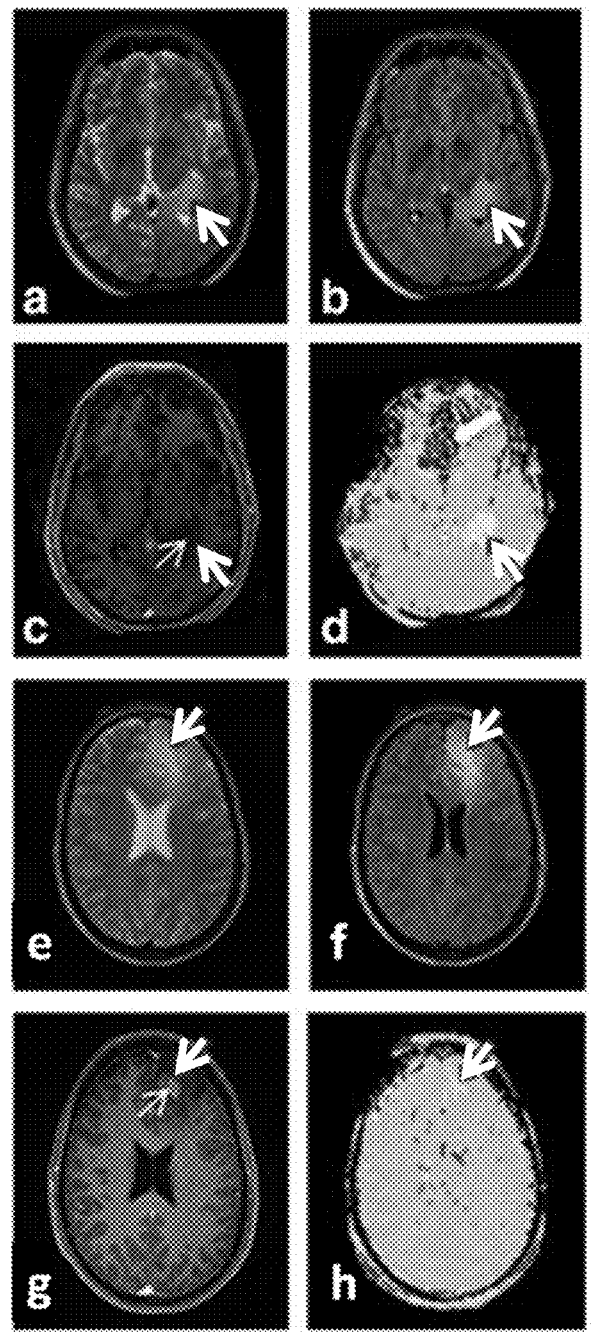
FIG. 8 shows APT-weighted and conventional MR images of a patient with a confirmed grade-3 anaplastic astrocytoma (Panels a, b, c, d) and APT images in accordance with the various embodiments and conventional MR images for a case with a confirmed grade-2 astrocytoma with mild gadolinium enhancement.
Figure 9:
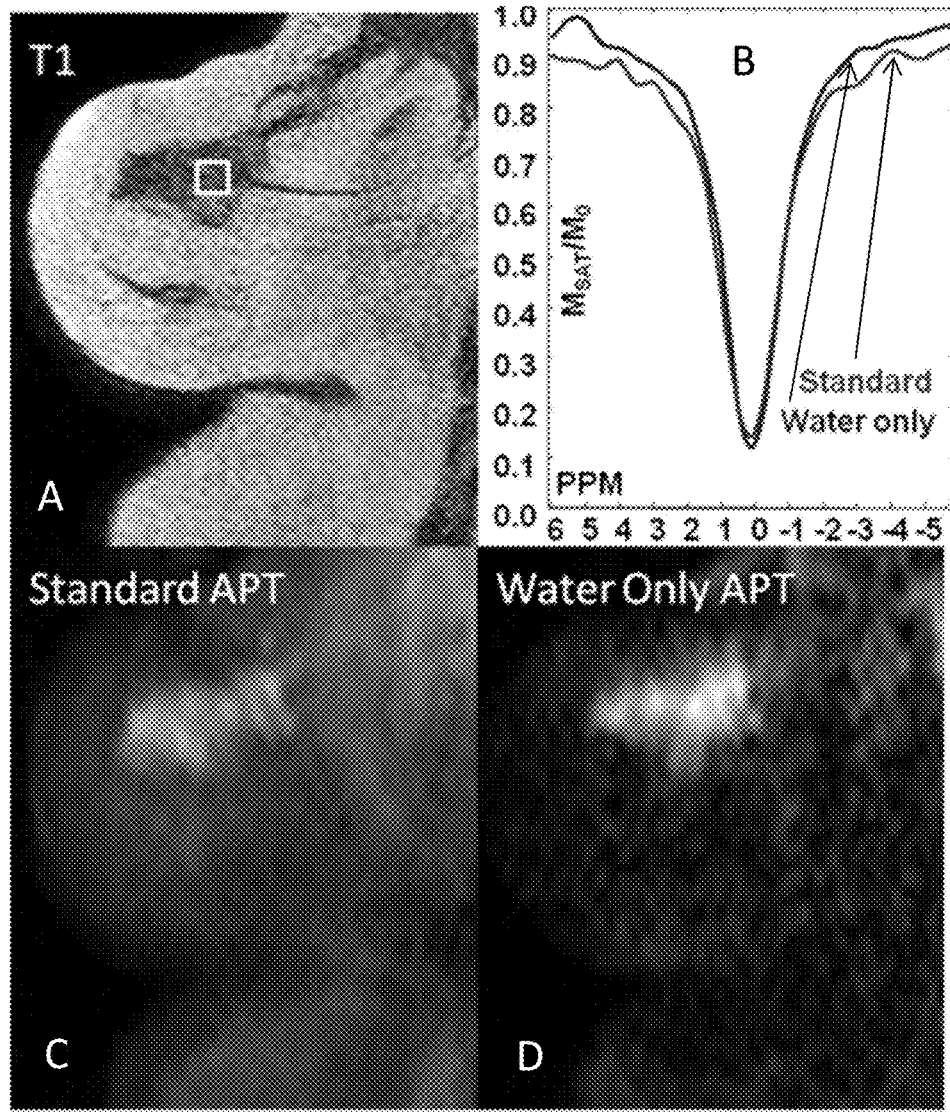
FIG. 9 shows in vivo results comparing standard APT and water-only APT in accordance with the various embodiments.

The APT method was included with a standard brain tumor protocol consisting T2-weighted imaging (panels a and e in FIG. 8), FLAIR (b and f in FIG. 8) and contrast-enhanced $T_1$-weighted imaging (panels c and g in FIG. 8) in 14 brain tumor patients. Histopathology confirmed 8 cases of high-grade gliomas and 6 low-grade gliomas. All high-grade cases showed markedly increased APT intensities even in 2 non-enhancing cases. Panels a, b, c, and d in FIG. 8 show APT-weighted and conventional MR images of a patient with a confirmed grade-3 anaplastic astrocytoma. This brain lesion showed no contrast enhancement and was initially presumed to be low-grade. However, APT-weighted hyperintensity was clearly visible in the lesion, which predicted the high-grade pathology. This patient was found to have a high-grade glioma on histopathology when tissue from the region of increased APT-weighted intensity was sampled. These results suggest that the APT-weighted hyperintensity (compared with the contralateral normal-appearing white matter) is a typical feature of high-grade gliomas. In addition, all six low-grade gliomas consistently showed low APT weighted signals. Panels e, f, g, and h in FIG. 7 show APT-weighted and conventional MR images for a case with a confirmed grade-2 astrocytoma with mild gadolinium enhancement. The APT-weighted signal intensity was low within the lesion, consistent with features of a low-grade glioma. Histopathology later showed that this was a case of diffuse astrocytoma, containing scattered gemistocytic tumor cells. These results suggest that APT measurement can be a biomarker of the malignancy and density of tumor cells.

However, the lipid suppression method used in this brain tumor study is not sufficient for breast imaging as fat tissues in the breast are more heterogeneous. Therefore, in the various embodiments, the conventional lipid suppression was replaced with water-only excitation for APT imaging in the breast, as discussed above with respect to FIG. 2. The same frequency SG selective excitation pulse replaced lipid suppression and standard slice selective excitation. The other MRI parameters were: TE/TR=36 ms/2.5 s, FOV=160×160×40 mm$^3$ (AP×FH×RL); resolution=2×4×4 mm³; A full z-spectrum acquisition at 26 offsets (M₀, 0-6 ppm in 0.5 ppm step size) was used. Total scan time=4:28 min. Panels A and B in FIG. 7 show a T1-weighted image and two z-spectra from the marked location. Panels C and D in FIG. 7 show (with identical intensity scales) M₀ images acquired with both APT methods. The water-only APT method clearly exceeds the standard method for the negligible amount of residual lipid signals.

E. MRS with Choline Excitation.

Figure 10:
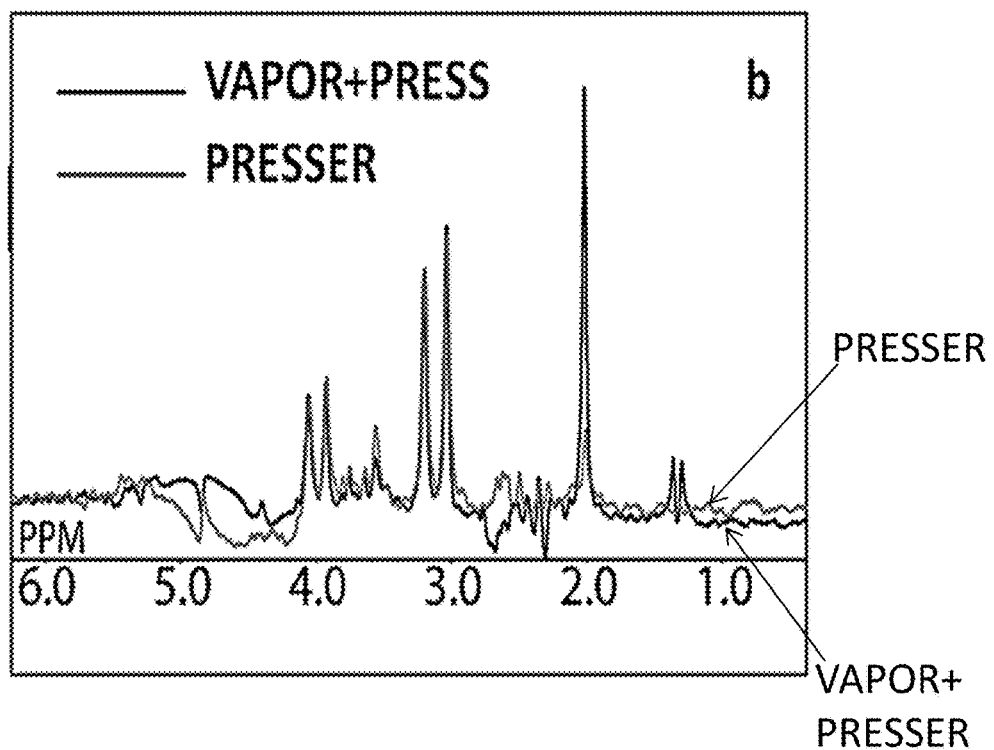
FIG. 10 shows a spectral comparison of PRESS and PRESSER in a phantom.

For MRS, a standard PRESS sequence was modified to provide a PRESSER sequence in which three slice selective refocusing pulses defined a volume and a frequency selective 90 degree pulse specified a desired spectral region to excite, as described above with respect to FIG. 3. The PRESSER sequence was intended to excite a small spectral window around the Choline resonance frequency. The standard press sequence was also applied. A direct comparison of these spectroscopy methods, using a solution phantom of neuro-metabolites (FIG. 10), shows that both methods correctly acquired the Choline signal at 3.2 ppm while the spectrum from PRESSER shows diminishing spectral peaks in both upfield and downfield directions. For example, the signals around 2.0 ppm, associated with water, are diminished significantly with PRESSER. Further, the signals at around 1.3 ppm, associated with fat, are also significantly diminished with PRESSER.

F. Further Evaluation of Water Selective DWI

A test-retest study was conducted, using in vivo scans, to investigate if the added complexity of the water selective DWI method of the various embodiments compromised reproducibility. All in vivo scans were performed on a 3T whole body scanner with a 16 channel phased array breast coil (Achieva, Philips Healthcare, Best, the Netherlands). Ten healthy volunteers, were scanned on two separate visits for this study. Eight subjects returned for their second scan in 1 or 2 days while two subjects returned after seven days as permitted by their schedules.

Spectrally selective excitation was implemented in a diffusion weighted spin echo (SE) sequence with a Gaussian excitation pulse (BW=200 Hz) and two adiabatic full passage (AFP) pulses. The arrangement of the diffusion gradients was adapted to one extra 180° pulse and increased crusher gradients. Other parameters were: TE/TR=76 ms/1 s, slice thickness=3 mm, FOV=(192 mm)2 (FH×AP), resolution=(2 mm)2, b-factors=0, 50, 600 s/mm², NSA=10, scan time=1:41 min. For image-based shimming, a 3D sagittal B0 mapping method and a numerical optimization procedure were used. Shimming and center frequency conditions for every scan were confirmed during pre-scan where water peak and various fat peaks were assigned according to their respective spectral locations.

Figure 12A:
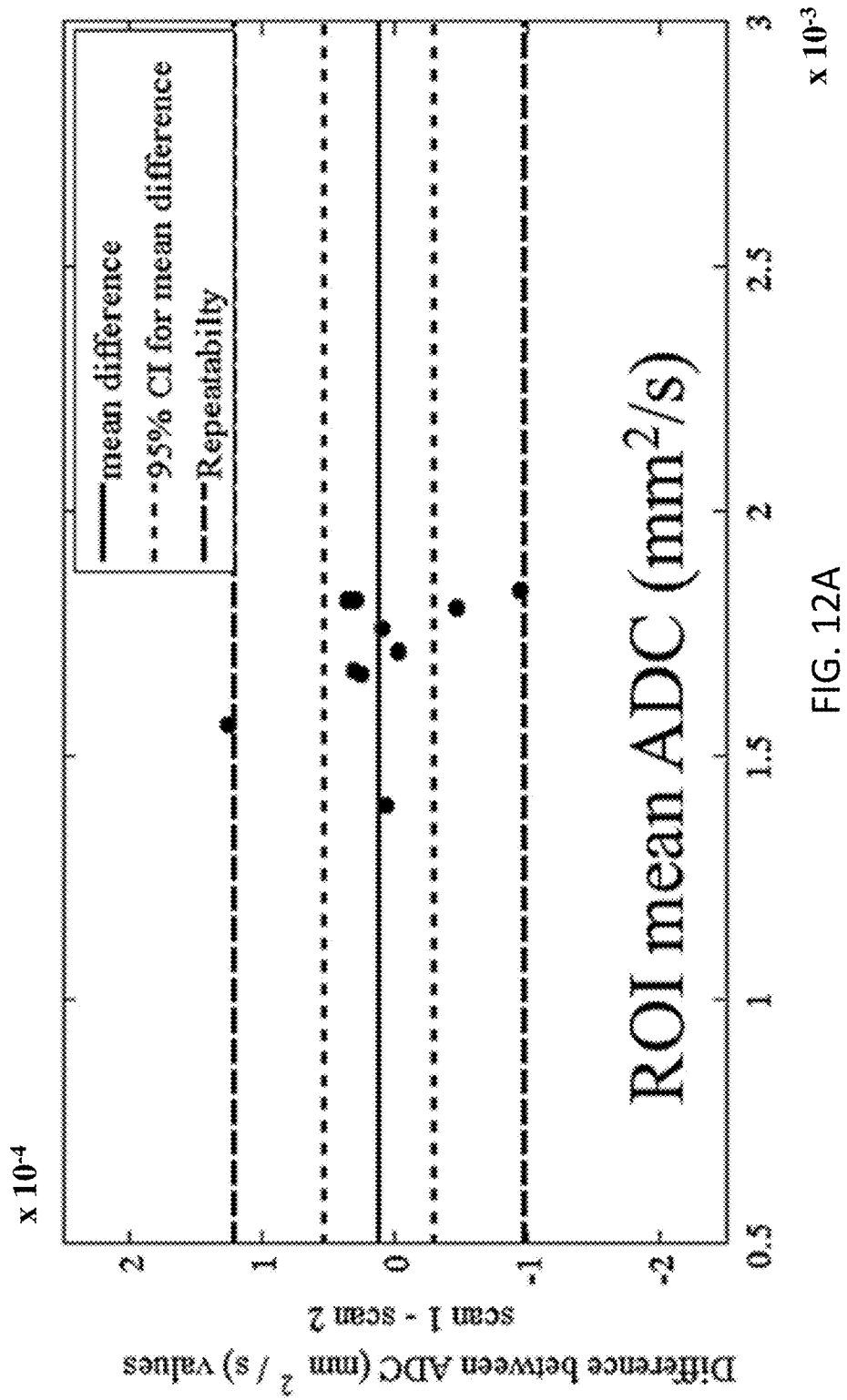
FIGS. 12A and 12B show Bland-Altman plots for the mean and median ADC values.
Figure 12B:
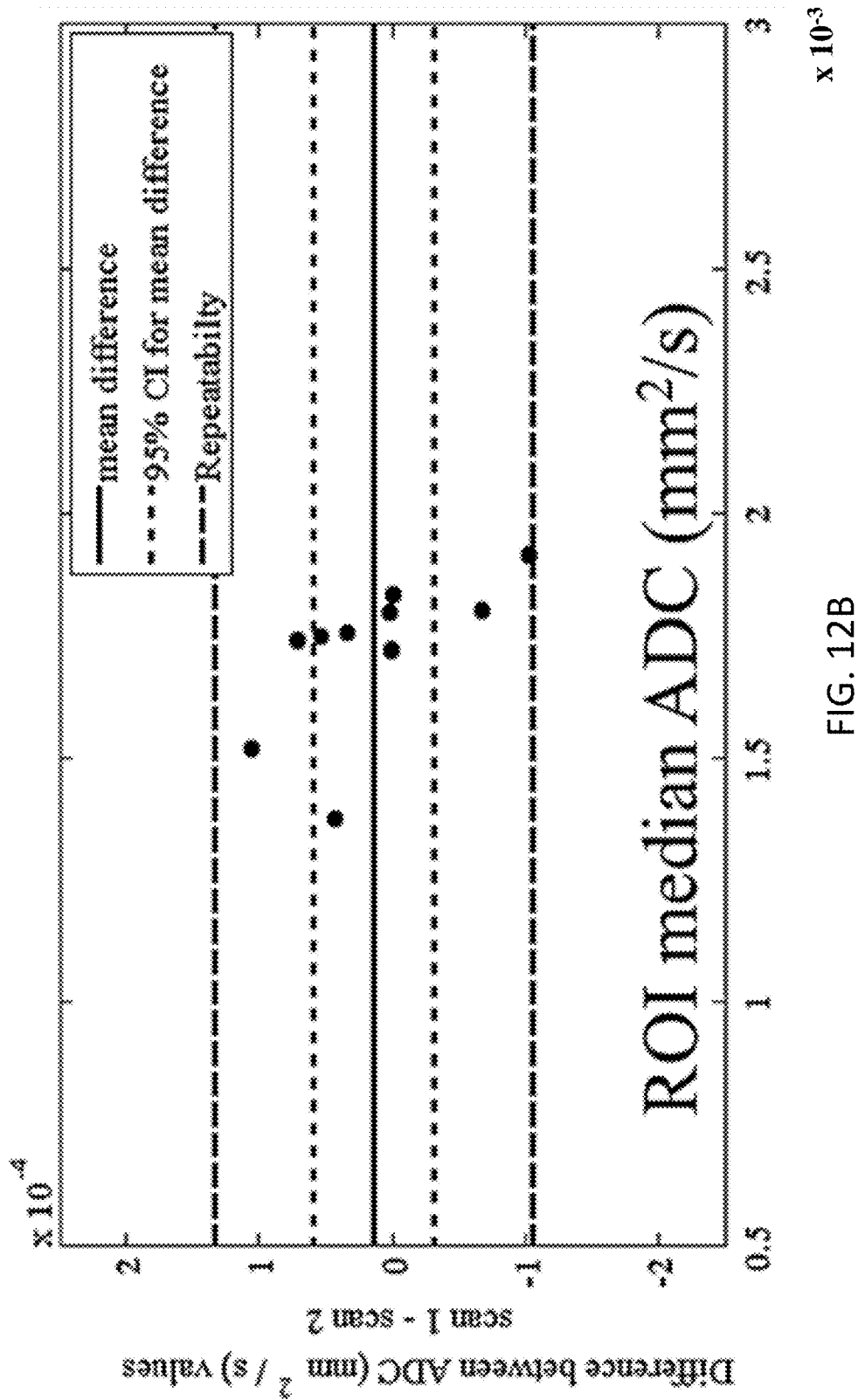

FIGS. 11A and 11B show DWI images and FIGS. 11C and 11D show ADC (mm²/s) maps, where FIGS. 11A-11D were obtained using 2 scans from one subject. Regions of interests (ROI) in ADC maps were masked using DW images. Both mean and median ADC values were calculated within the ROI for each subject. Measurements from ten subjects are shown in the Bland-Altman plots in FIGS. 12A and 12B for the mean and median ADC values, respectively. Mean differences, 95% CI and repeatability ranges are displayed as solid, dotted and dashed lines, respectively.

Figure 13:
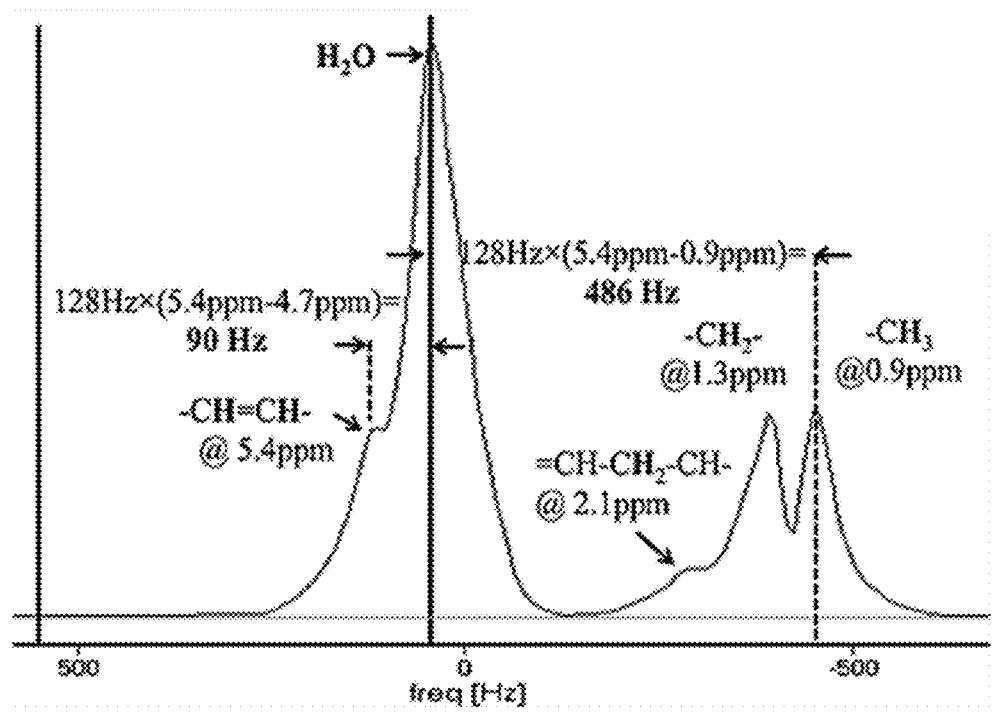
FIG. 13 shows water selection among fat resonances in breast tissue.

These results show that the selectivity of the water signal by the method of the various embodiments depends on the bandwidth of the excitation pulse and the spectral separations of various fat resonances from the water resonance relative to the residual field inhomogeneity. Human adipose tissues consist of several resonances at 0.9 ppm, 1.3 ppm, 2.1 ppm, 2.8 ppm and 5.4 ppm. With an excitation bandwidth of 200 Hz, strong fat signals, except those from olefinic protons "—CH=CH—" at 5.4 ppm, are excluded. The frequency separation between 5.4 ppm and 4.7 ppm at 3T is approximately 90 Hz, which is comparable to the line width of water from a breast. This is evident in FIG. 13, illustrating water selection among fat resonances in breast tissue. As shown in FIG. 13, the fat peak at 5.4 ppm falls within the frequency range of the water signal. Therefore, excluding this fat resonance without compromising water selectivity is not feasible with our method or any fat suppression method at 3T. In addition, human adipose tissue also consists of a non-negligible amount of water so zero signal is not expected from fat regions (as shown in FIGS. 11A and 11B).

Regarding the ADC variations observed, the main source results from the difference between slice locations from two visits. As slimmer subjects have considerable room to position themselves in the coil used, duplicating the exact slice position and angle in the second visit was difficult. This probably caused the small ADC variations for the eight subjects that returned in less than two days. For the two subjects that returned after 7 days, it is observed the two highest variations in both mean and median ADC. This finding is consistent with a previous study of ADC changes with phase of the menstrual cycle. These results demonstrated water selective excitation as a feasible alternative to existing methods of fat suppression and the added complexity of the sequence did not reduce the reliability of the diffusion measurements.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method for a magnetic resonance (MR) analysis of a biological structure, comprising:
   generating a spin echo imaging pulse sequence for acquisition comprising a spectrally selective excitation pulse, a plurality of refocusing pulses subsequent to the excitation pulse, and a pair of diffusion gradient pulses, the excitation pulse selected to excite water signals in the biological structure without exciting lipid signals in the biological structure associated with at least one dominant resonance for lipids;
   subsequent to the imaging pulse sequence, collecting echo signals from the biological structure; and
   producing at least one diffusion weighted MR image based on the echo signals,
   wherein the plurality of refocusing pulses comprises at least one pair of adiabatic inversion pulses, and wherein the pair of diffusion gradient pulses are applied prior to and subsequent to one of the plurality of refocusing pulses.

2. The method of claim 1, wherein the excitation pulse comprises a pulse with an amplitude between 0.1 µT and 30µ, a center frequency between less than 12.0 ppm, a bandwidth between 20 Hz and 525 Hz, and a duration between 4 ms and 100 ms.

3. The method of claim 1, wherein the excitation pulse is one of a Gaussian pulse, a sinc Gaussian pulse, a minimal phase pulse, or an adiabatic half passage (AHP) pulse.

4. The method of claim 1, wherein the biological structure comprises breast tissue.

5. The method of claim 1, wherein a duration of each of the pair of diffusion pulses is longer than a duration of an associated one of the plurality of refocusing pulses.

6. A method for a magnetic resonance (MR) analysis of a biological structure, comprising:
   generating a first spin echo pulse sequence for acquisition comprising at least one saturation pulse followed by a spectrally selective excitation pulse, the at least one saturation pulse selected for saturating protons for protein species in the biological structure, and the excitation pulse selected to excite water signals in the biological structure without exciting lipid signals in the biological structure associated with at least one dominant resonance for lipids;
   applying a plurality of refocusing pulses subsequent to the first spin each pulse sequence;
   applying pair of diffusion gradient pulses;
   subsequent to the applying, collecting echo signals from the biological structure; and
   producing at least one saturation transfer MR image based on the echo signals,
   wherein the plurality of refocusing pulses comprises at least one pair of adiabatic inversion pulses, and wherein the pair of diffusion gradient pulses are applied prior to and subsequent to one of the plurality of refocusing pulses.

7. The method of claim 6, wherein the excitation pulse comprises a pulse with an amplitude between 0.1 µT and 30 µT, a center frequency between 0 ppm and 12.0 ppm, a bandwidth between 20 Hz and 525 Hz, and a duration between 4 ms and 100 ms.

8. The method of claim 6, wherein the excitation pulse is one of a Gaussian pulse, a sinc Gaussian pulse, a minimal phase pulse, or an adiabatic half passage (AHP) pulse.

9. The method of claim 6, further comprising, prior to the producing, repeating the applying and the collecting a plurality of times.

10. The method of claim 6, wherein the biological structure comprises breast tissue.

11. The method of claim 6, wherein a duration of each of the pair of diffusion pulses is longer than a duration of an associated one of the plurality of refocusing pulses.

12. A method for a magnetic resonance (MR) analysis of a biological structure, comprising:
   generating a spin echo imaging pulse sequence for acquisition comprising a spectrally selective excitation pulse and at least three refocusing pulses subsequent to the excitation pulse, the excitation pulse selected to excite signals for at least one particular chemical compound in the biological structure without exciting signals for at least one other particular chemical compound in the biological structure associated with at least one dominant resonance for the at least one other particular chemical compound, and a pair of diffusion gradient pulses configured to provide spatial localization in three dimensions;
   subsequent to the imaging pulse sequence, collecting echo signals from the biological structure; and
   producing at least one MR image or an MR spectrum based on the echo,
   wherein the plurality of refocusing pulses comprises at least one pair of adiabatic inversion pulses, and wherein the pair of diffusion gradient pulses are applied prior to and subsequent to one of the at least three refocusing pulses.

13. The method of claim 12, wherein the excitation pulse comprises a pulse with an amplitude between 0.06 µT and 30 µT, a center frequency between 0 ppm and 12.0 ppm, a bandwidth between 10 Hz and 260 Hz, and a duration between 160 ms and 8.5 ms.

14. The method of claim 12, wherein the excitation pulse is one of a Gaussian pulse, a sinc Gaussian pulse or a minimal phase pulse.

15. The method of claim 12, wherein a duration of each of the pair of diffusion pulses is longer than a duration of an associated one of the at least three refocusing pulses.

* * * * *

UNITED STATES PATENT AND TRADEMARK OFFICE
CERTIFICATE OF CORRECTION

PATENT NO. : 9,775,557 B2  
APPLICATION NO. : 14/244462  
DATED : October 3, 2017  
INVENTOR(S) : He Zhu Page 1 of 1

It is certified that error appears in the above-identified patent and that said Letters Patent is hereby corrected as shown below:

On the Title Page

Item (12), should read:
Zhu

Item (72), Inventor:
Please replace "Zhu He" with --He Zhu--

In the Specification

In Column 1, after the section entitled GOVERNMENT LICENSE RIGHTS, Lines 17-20 should be replaced with the following:
--This invention was made with government support under grant numbers CA142565 and CA068485 awarded by the National Institutes of Health. The government has certain rights in the invention.--

Signed and Sealed this  
Thirtieth Day of June, 2020

Andrei Iancu  
*Director of the United States Patent and Trademark Office*